US012778731B2

(12) United States Patent
Arai et al.

(10) Patent No.: US 12,778,731 B2
(45) Date of Patent: Nov. 3, 2026

(54) JAW MOVEMENT ANALYSIS SYSTEM

(71) Applicants: NIHON UNIVERSITY, Tokyo (JP); J. MORITA MFG. CORP., Kyoto (JP)

(72) Inventors: Yoshinori Arai, Tokyo (JP); Toshimitsu Iinuma, Tokyo (JP); Fuyuki Yamada, Kyoto (JP); Hideki Yoshikawa, Kyoto (JP)

( * ) Notice: Subject to any disclaimer, the term of this patent is extended or adjusted under 35 U.S.C. 154(b) by 1142 days.

(21) Appl. No.: 17/846,013

(22) Filed: Jun. 22, 2022

(65) Prior Publication Data

US 2022/0323189 A1 Oct. 13, 2022

Related U.S. Application Data

(63) Continuation of application No. PCT/JP2020/046769, filed on Dec. 15, 2020.

(30) Foreign Application Priority Data

Dec. 25, 2019 (JP) ................................ 2019-234444

(51) Int. Cl.
*A61C 19/045* (2006.01)
*A61B 5/00* (2006.01)
(Continued)

(52) U.S. Cl.
CPC ............ *A61C 19/045* (2013.01); *A61B 5/228* (2013.01); *A61B 5/682* (2013.01); *A61B 5/7267* (2013.01);
(Continued)

(58) Field of Classification Search
CPC ....... A61C 19/045; A61B 5/228; A61B 5/682; A61B 5/7267; A61B 2562/0219;
(Continued)

(56) References Cited

U.S. PATENT DOCUMENTS 10,373,716 B2 * 8/2019 Vleugels ................ G16H 40/63
10,888,265 B2 * 1/2021 Edwards ................ A61B 5/228
(Continued)

FOREIGN PATENT DOCUMENTS

JP 2012-191994 10/2012
JP 2014-131426 7/2014
(Continued)

OTHER PUBLICATIONS

Farooq, M., et al. "A Comparative Study of Food Intake Detection Using Artificial Neural Network and Support Vector Machine" IEEE 12th Int'l Conf. on Machine Learning & Applications, pp. 153-157 (2013) (Year: 2013).*
(Continued)

*Primary Examiner* — Jay Hann
(74) *Attorney, Agent, or Firm* — SHIPWAY IP

(57) ABSTRACT

A jaw movement analysis system includes circuitry that is configured to acquire chewing information including time-series information that represents a jaw movement of a user chewing a bite of food, and to determine an attribute of the food having been chewed by the user based on the chewing information acquired and based on an analysis model. The analysis model is generated by machine learning based on training data including first information that includes time-series information indicating a past jaw movement during a chewing of a bite of food, and second information that indicates an attribute of the food chewed during the past jaw movement associated with the first information.

18 Claims, 13 Drawing Sheets

(51) Int. Cl.

| | |
|---|---|
| ***A61B 5/22*** | (2006.01) |
| ***G16H 50/20*** | (2018.01) |
| ***G16H 50/70*** | (2018.01) |

(52) U.S. Cl.
CPC ............. *G16H 50/20* (2018.01); *G16H 50/70* (2018.01); *A61B 2562/0219* (2013.01)

(58) Field of Classification Search
CPC ............ A61B 5/486; A61B 2560/0209; A61B 2560/0214; A61B 2560/0456; A61B 5/7214; A61B 5/11; G16H 50/20; G16H 50/70; G16H 30/20; G16H 30/40; G16H 40/63; G16H 50/30
See application file for complete search history.

(56) References Cited

U.S. PATENT DOCUMENTS

| | | | | |
|---|---|---|---|---|
| 11,013,430 | B2 * | 5/2021 | Tanriover | A61B 5/7207 |
| 11,064,942 | B1 * | 7/2021 | Catani | A61B 5/14532 |
| 11,087,870 | B2 * | 8/2021 | Barthelaix | G08B 5/36 |
| 11,234,644 | B2 * | 2/2022 | Kochura | A61B 5/4205 |
| 2012/0172677 | A1 | 7/2012 | Logan et al. | |
| 2016/0073953 | A1 * | 3/2016 | Sazonov | A61B 5/1107 600/590 |
| 2019/0038186 | A1 | 2/2019 | Tanriover et al. | |

FOREIGN PATENT DOCUMENTS

| | | |
|---|---|---|
| JP | 2018-151578 | 9/2018 |
| JP | 2019-067281 | 4/2019 |
| KR | 10-2011-0092863 | 8/2011 |

OTHER PUBLICATIONS

Duyck, J., et al. "Impact of Denture Cleaning Method and Overnight Storage Condition on Denture Biofilm Mass and Composition: A Cross-Over Randomized Clinical Trial" PLoS ONE, vol. 11, issue 1, e0145837 (2016) (Year: 2016).*

Farooq, M. & Sazonov, E. "A Novel Wearable Device for Food Intake and Physical Activity Recognition" Sensors, vol. 16, 1067 (2016) (Year: 2016).*

Lee, K.S. "Food Intake Detection Using Ultrasonic Doppler Sonar" IEEE Sensors J., vol. 17, No. 18 (2017) (Year: 2017).*

International Search Report dated Mar. 9, 2021 for PCT/JP2020/046769.

International Preliminary Report on Patentability with Written Opinion dated Jul. 7, 2022 for PCT/JP2020/046769.

Huang Qianyi et al., "Your Glasses Know Your Diet: Dietary Monitoring Using Electromyography Sensors", IEEE Internet of Things Journal, IEEE, USA, vol. 4, No. 3, Jun. 1, 2017, p. 705-p. 712.

Oliver Amft, "A wearable earpad sensor for chewing monitoring", Sensors, 2010 IEEE, IEEE, Piscataway, NJ, USA, Nov. 1, 2010, p. 222-p. 227.

Extended Search Report in corresponding European Application No. 20906578.8, dated Jan. 3, 2024.

* cited by examiner

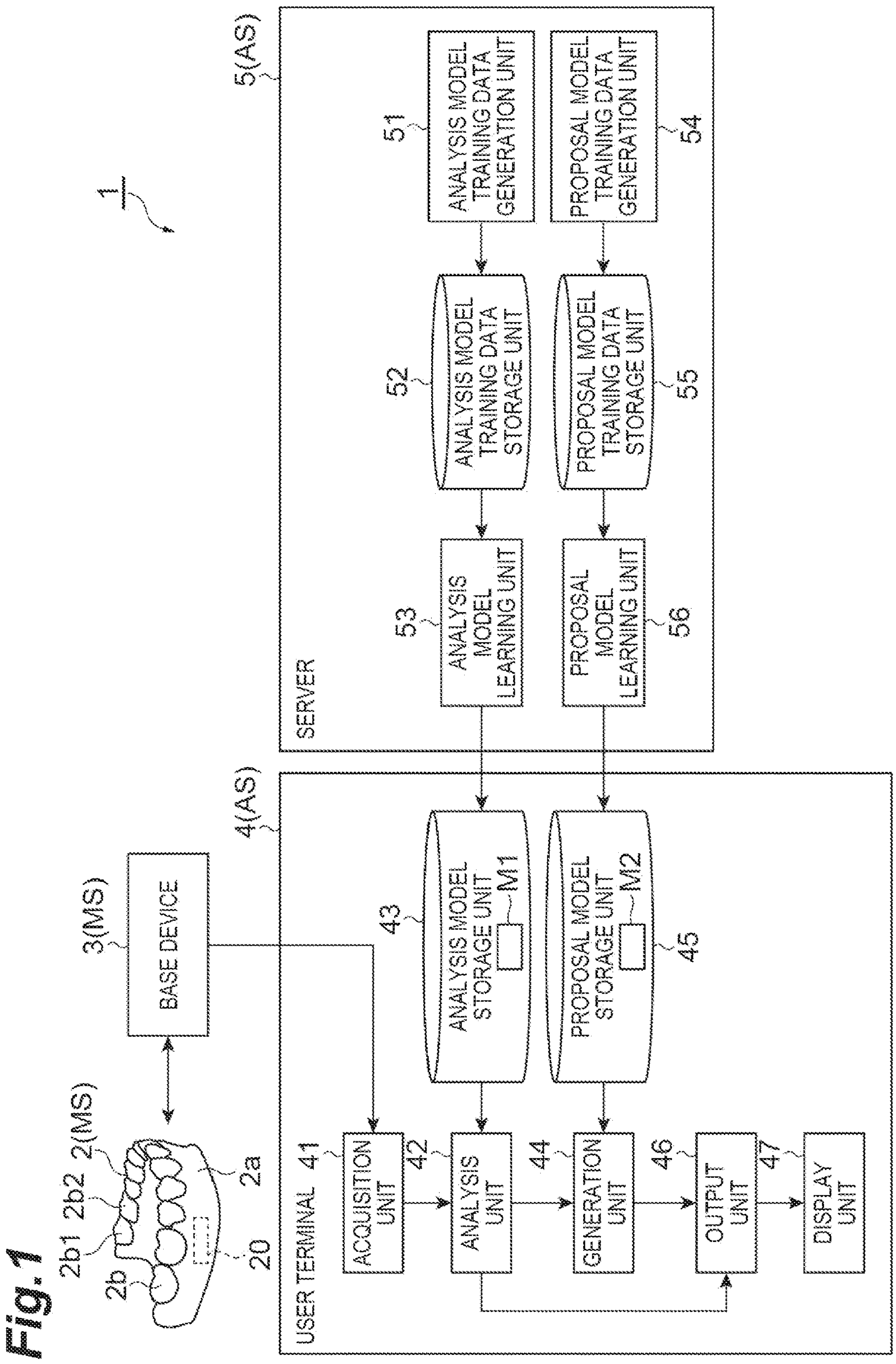
Fig. 1
1
5(AS)
SERVER
51
ANALYSIS MODEL TRAINING DATA GENERATION UNIT
52
ANALYSIS MODEL TRAINING DATA STORAGE UNIT
53
ANALYSIS MODEL LEARNING UNIT
54
PROPOSAL MODEL TRAINING DATA GENERATION UNIT
55
PROPOSAL MODEL TRAINING DATA STORAGE UNIT
56
PROPOSAL MODEL LEARNING UNIT
4(AS)
USER TERMINAL
41
ACQUISITION UNIT
42
ANALYSIS UNIT
43
ANALYSIS MODEL STORAGE UNIT
M1
44
GENERATION UNIT
45
PROPOSAL MODEL STORAGE UNIT
M2
46
OUTPUT UNIT
47
DISPLAY UNIT
3(MS)
BASE DEVICE
2(MS)
2a
2b
2b1
2b2
20

JAW MOVEMENT ANALYSIS SYSTEM

CROSS-REFERENCE TO RELATED APPLICATIONS

This application is a continuation application of PCT/JP2020/046769, filed on Dec. 15, 2020, which claims the benefit of priority of Japanese Patent Application No. 2019-234444, filed on Dec. 25, 2019, the entire contents of which are incorporated herein by reference.

BACKGROUND

Japanese Unexamined Patent Publication No. 2012-191994 describes a device that performs analysis of a behavior of an animal, including a human, using information obtained from an oral sensor provided in an oral cavity of the animal.

SUMMARY

Information on food ingested (chewed) by a user can be obtained as an analysis result from a jaw movement of the user at the time of eating, in order to advise the user on dietary habits based on the analysis result, for example.

In the afore-mentioned analysis device, various types of information must be obtained in advance for collation with the information obtained from the oral sensor (information on oral operations, information on vibration generated in the oral cavity, information on vibration generated in a living body, or the like). It may be relatively complex and time-consuming to acquire and accumulate such various types of information in advance.

A dietary habits assessment system (or jaw movement analysis system) according to some examples of the present disclosure, includes a circuitry configured to acquire chewing information including time-series information representing a jaw movement of a user chewing a bite of food, and to determine an attribute of the food having been chewed by the user based on the chewing information and based on an analysis model.

The analysis model is generated by machine learning based on training data including first information and second information. The first information is time-series information indicating a past jaw movement during a chewing of a bite of food. The second information indicates an attribute of the food chewed during the past jaw movement associated with the first information.

In the dietary habits assessment system, the attribute of the food determined to have been chewed by the user is acquired by using the analysis model generated by machine learning. In some examples, the analysis model may be generated by machine learning using training data obtained from past meals of the user who is an analysis target, such that the past jaw movement may be a past jaw movement performed by the user. Accordingly, an analysis result (e.g., the attribute of the food determined to have been chewed by the user) may be obtained more easily and more accurately by using the analysis model that includes learned characteristics of the jaw movement of the user at the time of eating.

In some examples, the past jaw movement is a past jaw movement performed by an unspecified user.

In such examples, the analysis model may be generated by machine learning using training data obtained from past meal of the unspecified user. Accordingly, an analysis result (e.g., the attribute of the food determined to have been chewed by the user) may be obtained more easily and more accurately by using the analysis model. Further, the analysis model can be shared among a plurality of users, without the need to generate and manage a separate analysis model for each user. In addition, it may be easier to collect training data for the analysis model.

In some examples, the training data further includes profile information of the unspecified user, and the dietary habits assessment system may be further configured to acquire profile information indicating an attribute of the user, such that the food attribute is determined additionally based on the profile information acquired. The jaw movement of the user at the time of eating may depend on the attribute (for example, a sex, age, or health condition) of the user. Accordingly, the attribute of the food having been chewed by the user may be determined more accurately by taking into consideration the attribute of the user.

In some examples, the analysis model may be a learned model generated by machine learning using training data including data corresponding to first chewing information, the first chewing information being time-series information indicating a jaw movement corresponding to a first chewing motion (or first chewing operation) in the first information, data corresponding to second chewing information, the second chewing information being time-series information indicating a jaw movement corresponding to a second chewing motion (or second chewing operation) in the first information, and the second information. The dietary habits assessment system may extract first chewing information and second chewing information from the chewing information associated with the bite of food chewed by the user, to determine the attribute of the food having been chewed. For example, in may be easier to identify the attribute of the food having been chewed from the jaw movements corresponding to the first chewing motion and the second chewing motion during the chewing of the bite of food. Accordingly, the attribute of the food having been chewed by the user may be determined more accurately, by generating the analysis model based on the jaw movement corresponding to the first chewing motion and the second chewing motion.

In some examples, the dietary habits assessment system may acquire the chewing information from jaw movement information detected by a sensor provided in a lower jaw denture that is mountable on a lower jaw of the user. According to this configuration, the jaw movement information that is the basis of the chewing information may be acquired on a daily basis, by using the sensor. Further, the jaw movement information may be suitably acquired while minimizing a burden on the user, by using the sensor provided in the denture worn by the user during daily life, including during the time of eating.

The jaw movement information may include information indicating temporal change in at least one of acceleration in triaxial directions and angular velocity in triaxial directions detected by the sensor. Additionally, the jaw movement information may further include information indicating temporal change in at least one of the acceleration in the triaxial directions and the angular velocity in the triaxial directions detected by a sensor provided in an upper jaw denture that is mountable on an upper jaw of the user. For example, when the user is in a vehicle such as a car or a train, there is concern that a vibration component from the vehicle may be detected by the sensor, so as to be erroneously detected as a jaw movement for eating. Further, when the user eats while in a vehicle, the vibration component from the vehicle may be incorporated as noise into the jaw movement of the user at the time of eating.

In some examples, the system may acquire only movement components indicating the jaw movements of the user as the chewing information by using not only a detection result of a sensor provided in a denture mounted on the lower jaw of the user, but also detection results of a sensor provided in a denture mounted on the upper jaw of the user. In some examples, the vibration component (that is, a component commonly contained in both the sensor of the upper jaw and the sensor of the lower jaw) from the vehicle may be cancelled out by obtaining a relative value of a detection result of the sensor of the lower jaw with respect to a detection result of the sensor of the upper jaw.

In the dietary habits assessment system, the food attribute may include at least one of a size, a hardness, and a type of food.

The dietary habits assessment system may further include a base device configured to store the denture removed from the lower jaw of the user. The base device may acquire the jaw movement information from the sensor by communicating with the sensor. In some examples, the user may set the denture in the base device, such that the jaw movement information is automatically transmitted from the base device to a device that analyzes the jaw movement information, to improve the convenience for the user in connection with the acquisition (uploading) of the jaw movement information from the sensor provided in the denture.

The base device may further include a charging device (or charger or charging unit) configured to charge the sensor. For example, the charging device may perform charging together with communication using a communication device (or communication unit), such that power of the sensor consumed during a communication operation using the communication device to be appropriately supplemented.

The base device may further include a cleaning device (or cleaner or cleaning unit) configured to clean the denture. For example, the base device can perform both transmission of the jaw movement information to a device that analyzes the jaw movement information and cleaning of the denture when the user sets the denture in the base device, so as to improve the convenience for the user.

BRIEF DESCRIPTION OF DRAWINGS

FIG. 1 is a block diagram illustrating a configuration of a dietary habits assessment system according to an example.

DETAILED DESCRIPTION

Figure 2:
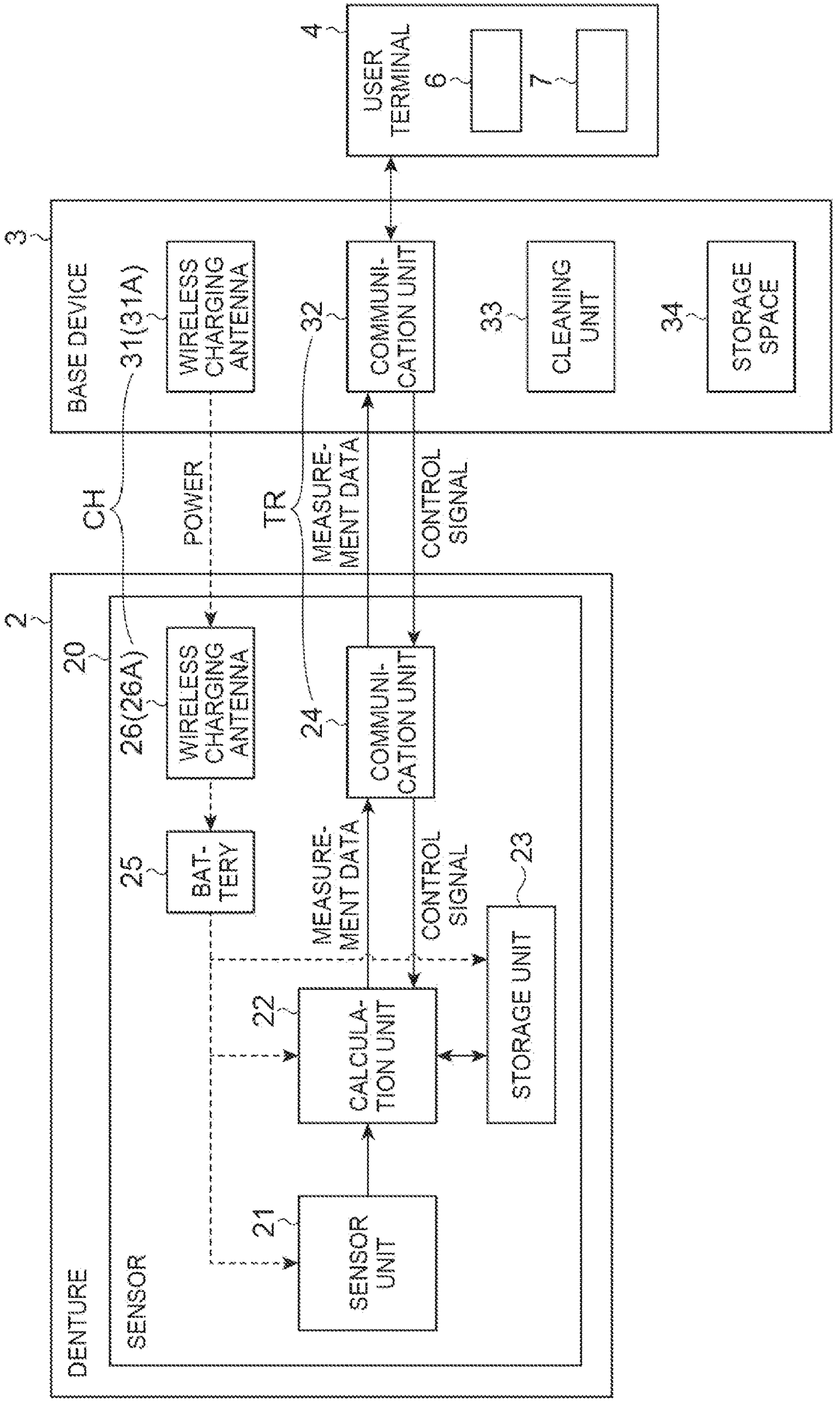
FIG. 2 is a block diagram illustrating a schematic configuration of a denture and a base device.

In the following description, with reference to the drawings, the same reference numbers are assigned to the same components or to similar components having the same function, and overlapping description is omitted.

Overall Configuration of Dietary Habits Assessment System

As illustrated in FIG. 1, a dietary habits assessment device 1 (also referred to herein as a "dietary habits assessment system" or "dietary habits estimation system" or "jaw movement analysis system") according to an example, includes a denture 2, a base device 3 (base 3), a user terminal 4, and a server 5. The denture 2 is mounted on a lower jaw of a denture wearer (hereinafter referred to as a "user"). The denture 2 has a function of acquiring measurement data regarding the jaw movement (jaw movement information) of the user at the time of eating. The base device 3 is a device that stores the denture 2 removed from the lower jaw of the user. The user terminal 4 is a terminal (e.g., computing device) that is used by the user. The user terminal 4 is, for example, a mobile terminal such as a smartphone or a tablet owned by the user. Alternatively, the user terminal 4 may be, for example, a personal computer installed, for example, at a home of the user. The user terminal 4 mainly has a function of analyzing the measurement data acquired by the denture 2 and a function of generating proposal information (or recommendation information) related to eating habits for the user on the basis of the analysis result. The server 5 is a device that generates an analysis model to be used when the user terminal 4 analyzes the measurement data and a proposal model (or recommendation model) to be used when the user terminal 4 generates the proposal information, and provides the generated analysis model and the generated proposal model to the user terminal 4. The denture 2 and the base device 3 may form an actual measurement device MS that actually measures the jaw movement of the user. Further, the user terminal 4 and the server 5 form a calculation device AS that performs analysis (calculation) based on the measurement data.

Configuration of Denture

As illustrated in FIG. 1, the denture 2 includes a base portion 2*a* mounted on the lower jaw of the user, and a tooth portion 2*b* (teeth) detachably provided with respect to the base portion. Further, a sensor 20 is built into the denture 2, as illustrated in FIG. 2. The sensor 20 includes, for example, a circuit such as a processor (for example, a CPU) and a memory (for example, a ROM or a RAM) mounted on a board (not illustrated). The sensor 20 includes a sensor unit 21, a calculation unit 22, a storage unit 23, a communication unit 24, a battery 25, and a wireless charging antenna 26. In one configuration example, the calculation unit 22 includes circuits such as a processor (for example, a CPU) and a memory (for example, a ROM and a RAM) mounted on a board (not illustrated), and the storage unit 23 includes, for example, an electronic storage device such as a memory chip.

The sensor unit 21 includes various sensors for detecting movements of the upper and lower jaws, or a movement of the lower jaw of the user. For detection of the movement of the upper and lower jaws, or of the lower jaw, it is possible to use a sensor that detects at least one property among an acceleration and an angular velocity of the movement of the upper and lower jaws, or of the lower jaw. For example, at least one of an acceleration sensor and an angular velocity sensor may detect the movement. As the acceleration sensor, a sensor capable of measuring accelerations in triaxial directions is suitable. Further, since rotation elements other than a simple uniaxial rotation are often incorporated into the movement of the lower jaw, a sensor capable of measuring angular velocities in triaxial directions is suitable for the angular velocity sensor. According to examples, the sensor unit 21 includes an acceleration sensor that detects acceleration in each of triaxial directions (an X-axial direction, a Y-axial direction, and a Z-axial direction). In this case, the sensor unit 21 continuously detects the acceleration according to a movement (a jaw movement) of the lower jaw of the user. However, a configuration of the sensor unit 21 is not limited to the above. For example, the sensor unit 21 may include an angular velocity sensor (gyro sensor) that detects each angular velocity in the triaxial directions instead of the acceleration sensor, or may include both the acceleration sensor and the angular velocity sensor.

The calculation unit 22 acquires the measurement data (e.g., triaxial acceleration data indicating respective accelerations in the triaxial directions) continuously acquired by the sensor unit 21, and stores the measurement data in the storage unit 23. In some examples, the measurement data is time-series information indicating temporal change in acceleration according to the jaw movement of the user. In some examples, the sensor unit 21 may include an angular velocity sensor, such that the measurement data may include time-series information indicating a temporal change in angular velocity according to the jaw movement of the user. The storage unit 23 is provided by, for example, the above-described memory. However, the measurement data is not limited to the above example, and may be, for example, time-series information indicating temporal change in speed of the jaw movement. Further, the calculation unit 22 may include a time counting function. For example, when the calculation unit 22 is provided by a processor or the like, the calculation unit 22 can be configured to have a timer and counter built thereinto, like many processors. This timer and counter can be used for time allocation of the time-series information.

The calculation unit 22 adds an acquisition time of the measurement data to the measurement data at each point in time acquired by the sensor unit 21, for example, using the timer and counter described above. The calculation unit 22 stores the measurement data to which the acquisition time has been added in the storage unit 23. Accordingly, the time-series information in which the pieces of measurement data at respective point in time are arranged in order of acquisition time is stored in the storage unit 23.

Further, when the denture 2 is removed from the lower jaw of the user and set in the storage space 34 provided in the base device 3, the calculation unit 22 executes processing according to a control signal transmitted from the base device 3. For example, the calculation unit 22 reads the measurement data stored in the storage unit 23 and transmits the measurement data to the base device 3 via the communication unit 24 or erases the measurement data stored in the storage unit 23.

Further, the calculation unit 22 may control an operation mode of the sensor unit 21 as follows. In some examples, the calculation unit 22 stores a pattern of an acceleration according to an eating operation of the user in advance. Such a pattern may be stored in the storage unit 23, for example. The calculation unit 22 may operate the sensor unit 21 in a power saving mode in which a sampling rate is relatively low (that is, a sampling period is relatively long) as an initial mode. Further, the calculation unit 22 may constantly monitor the measurement data continuously acquired by the sensor unit 21, and operate the sensor unit 21 in a data acquisition mode in which the sampling rate is higher (that is, the sampling people is shorter) than in the power saving mode, with the pattern of the acceleration (for example, an acceleration equal to or higher than a predetermined threshold value) according to the eating operation of the user as a trigger. Thereafter, the calculation unit 22 may switch the operation mode of the sensor unit 21 to the power saving mode again, with a predetermined set time (for example, 30 seconds) having elapsed from a point in time when the pattern of the acceleration according to the eating operation of the user is no longer detected, as a trigger.

Thus, it is possible to reduce an amount of power consumption of the sensor unit 21 by setting the operation mode of the sensor unit 21 in a period other than an eating time of the user to the power saving mode. As a result, it is possible to continuously acquire the measurement data even when the user continuously wears the denture 2 for a long time. Further, it is possible to acquire more accurate measurement data indicating the jaw movement of the user at the time of eating by setting the operation mode of the sensor unit 21 to the data acquisition mode at the time of eating by the user.

Alternatively, the calculation unit 22 may store a scheduled meal time period (for example, a time period corresponding to each of breakfast, lunch, snack, and dinner) of the user in advance, operate the sensor unit 21 in the power saving mode in a time period other than the scheduled meal time period, and operate the sensor unit 21 in the data acquisition mode in the scheduled meal time period. With such control of the operation mode, the same effect as the above-described effect can also be obtained. It is possible to use the above-described timer and counter or the like for the control regarding a scheduled meal time.

The communication unit 24 has a function of communicating with the base device 3 through wireless communication in a state in which the denture 2 is set in the storage space 34 of the base device 3. The communication unit 24 includes, for example, an antenna for information transmission and reception. Such wireless communication includes, for example, radio wave communication, optical communication, or sound wave communication. The radio wave communication is communication using, for example, Bluetooth (registered trademark) or Wi-Fi (registered trademark). The optical communication is communication using, for example, visible light or infrared rays. The sound wave communication is communication using, for example, ultrasonic waves. When the communication unit 24 receives the control signal from the base device 3, the communication unit 24 transmits the control signal to the calculation unit 22. Further, when the communication unit 24 receives the measurement data from the calculation unit 22, the communication unit 24 transmits the measurement data to the base device 3.

The battery 25 is a storage battery that supplies power to the sensor unit 21, the calculation unit 22, the storage unit 23, and the like. The wireless charging antenna 26 is a component for charging the battery 25. In a state in which the denture 2 is set in the storage space 34 of the base device 3, power is supplied from the base device 3 to the battery 25 via the wireless charging antenna 26. That is, the battery 25 is charged through wireless charging. Thus, in the example denture 2, since the battery 25 can be charged in a non-contact manner, it is not necessary to expose a circuit (charging terminals) for charging the battery 25 to the outside of the denture 2.

The communication operation with the base device 3 using the communication unit 24 may be executed together with an operation of charging the battery 25. As described above, both the communication operation and the charging operation may be performed in a state in which the denture 2 is set in the storage space 34 of the base device 3. Here, the communication operation using the communication unit 24 consumes corresponding power even when any one of the wireless communication schemes is adopted, but when the charging operation is performed at the same time as the communication operation, it is possible to appropriately supplement power required for the communication operation.

At least some (e.g., the sensor unit 21, the battery 25, and the like that are frequently replaced) of the respective units included in the sensor 20 described above may be embedded in a particular tooth of the tooth portion 2*b* of the denture 2. In this case, an electrical connection between the respective units of the sensor 20, that is, an electrical connection between a portion embedded in the tooth portion 2*b* (for example, the battery 25 embedded in an individual tooth portion 2*b*1 in the tooth portion 2*b*) and another portion (a portion embedded in the base portion 2*a* or a portion embedded in another tooth of the tooth portion 2*b*) may be secured, for example, at a boundary between the tooth portion 2*b* and the base portion 2*a*. According to the above configuration, replacement work of the respective units included in the sensor 20 is facilitated. For example, the sensor unit 21 may be replaced by removing the tooth portion 2*b* (for example, an individual tooth portion 2*b*2) in which the sensor unit 21 is embedded, from the base portion 2*a*, and mounting a new tooth portion 2*b* (a tooth portion such as individual tooth portion 2*b*2, that includes the new sensor unit 21) on the base portion 2*a*.

Configuration of Base Device

As illustrated in FIG. 2, the base device 3 includes a wireless charging antenna 31, a communication unit 32, and a cleaning unit (also referred to herein as a cleaner, a cleaning device or a washer device) 33. The base device 3 is provided, for example, at the home of the user. Regarding a storage function of the base device 3, the base device 3 further includes the storage space 34 for storing the denture 2.

The wireless charging antenna 31 wirelessly charges the battery 25 of the denture 2 in a state in which the denture 2 is set in the storage space 34 of the base device 3. For example, the wireless charging antenna 31 supplies power to the battery 25 via the wireless charging antenna 26 described above. The wireless charging antenna 31 operates as a charging unit (charger or charging device). For example, the wireless charging antenna 31 forms a charging unit 31A on the base device 3 side, and the wireless charging antenna 26 forms a charging unit 26A on the sensor 20 side. The charging unit 31A and the charging unit 26A form a charging unit CH.

The communication unit 32 has a function of communicating with the sensor 20 of the denture 2 and the user terminal 4. For example, the communication unit 32 communicates with the communication unit 24 of the denture 2 through wireless communication in a state in which the denture 2 is set in the storage space 34 of the base device 3. Further, the communication unit 32 communicates with the user terminal 4 through wire communication or wireless communication. For example, when the communication unit 32 receives a control signal indicating a request for measurement data from the user terminal 4, the communication unit 32 transmits the control signal to the communication unit 24 of the denture 2 set in the base device 3. When the communication unit 32 receives the measurement data from the communication unit 24, the communication unit 32 transmits the measurement data to the user terminal 4. Accordingly, the measurement data acquired by the sensor 20 of the denture 2 is transmitted to the user terminal 4 via the base device 3. In the user terminal 4, the measurement data is analyzed and proposal information corresponding to an analysis result is generated. The communication unit 32 is a communication unit on the base device 3 side, and the communication unit 24 is a communication unit on the sensor 20 side. The communication unit 32 and the communication unit 24 form a communication unit TR.

The cleaning unit 33 has a function of cleaning the denture 2 in a state in which the denture 2 is set in the storage space 34 of the base device 3. The cleaning unit 33 may actuate an operation of introducing a liquid containing a dedicated chemical into the storage space 34, an operation of cleaning a surface of the denture 2 by immersing the denture 2 in the liquid, and an operation of removing the liquid from the storage space 34 after the cleaning, and an operation of drying the denture 2. That is, the storage space 34 also serves as a cleaning space capable of cleaning the denture 2.

As described above, the base device 3 has a function of storing the denture 2, charging of the sensor 20, communicating with the sensor 20 (acquisition of the measurement data from the sensor 20, transferring the control signal to the calculation unit 22, and the like), and cleaning of the denture 2. This makes it possible for the user to perform the storage of the denture 2, the charging of the sensor 20, the acquisition of the measurement data from the sensor 20 (and transmission of the measurement data to the user terminal 4), and the cleaning of the denture 2, by removing the denture 2 from the lower jaw of the user before going to bed, and setting the denture 2 in the storage space 34 of the base device 3, for example. According to such a base device 3, it is possible to acquire the measurement data regarding the jaw movement in daily life of the user while minimizing a burden on the user.

Configuration of User Terminal

As illustrated in FIG. 1, the user terminal 4 includes an acquisition unit 41, an analysis unit 42, an analysis model storage unit 43, a generation unit 44, a proposal model storage unit (or recommendation model storage unit) 45, an output unit 46, and a display unit 47. With further reference to FIG. 2, the user terminal 4 is a computer device including a processor 6 (for example, a CPU), a memory or storage 7 (for example, a ROM and a RAM), and the like. The user terminal 4 may include a timer and counter, similar to the calculation unit 22 of the sensor 20. Each of the acquisition unit 41, the analysis unit 42, the generation unit 44, the output unit 46, and the display unit 47 may be provided by one or more circuits (e.g., circuitry), and the processor 6 may include some or all of these circuits. Each of the acquisition unit 41, the analysis unit 42, the generation unit 44, the output unit 46, and the display unit 47 may be provided in the processor or in a part thereof, and the circuitry may include the memory 7. The memory 7 may include one or more storage device storing processor-readable data and instructions to be executed by the processor 6 to carry out the operations of the acquisition unit 41, the analysis unit 42, the generation unit 44, the output unit 46, and/or the display unit 47.

The acquisition unit 41 acquires the measurement data regarding the jaw movement of the user at the time of eating. As described above, the acquisition unit 41 acquires the measurement data acquired (detected) by and stored in the sensor 20 of the denture 2 via the base device 3. However, the method of the acquisition unit 41 acquiring the measurement data is not limited to the above. For example, the acquisition unit 41 may acquire the measurement data by directly communicating with the sensor 20 (the communication unit 24) without communicating with the base device 3.

In some examples, the measurement data is time-series information (e.g., triaxial acceleration data) indicating temporal change in respective accelerations in the triaxial directions detected by the sensor 20 provided in the denture 2 mounted on the lower jaw of the user. The triaxial acceleration data is information indicating an X-axis component, a Y-axis component, and a Z-axis component of the accelerations at respective times continuously acquired by the sensor unit 21 in a predetermined sampling people.

For example, when the user sets the denture 2 in the storage space 34 of the base device 3 while sleeping, the acquisition unit 41 can acquire the measurement data for one day (e.g., a period from a time when the user wakes up and wears the denture 2 to a time when the user removes the denture 2 before going to bed) of the user. Here, the acquisition unit 41 may acquire all pieces of the measurement data (that is, data for one day) stored in the storage unit 23 of the sensor 20, or may acquire only measurement data (e.g., measurement data at the time of eating by the user) acquired in the data acquisition mode by the sensor unit 21. For example, the acquisition unit 41 may transmit a control signal for requesting only the measurement data acquired in the data acquisition mode to the sensor 20 (the calculation unit 22) via the base device 3, and acquire only the measurement data acquired in the data acquisition mode from the sensor 20. According to the latter, only data necessary for analysis in the analysis unit 42 (e.g., measurement data at the time of eating by the user) as described further below, can be efficiently acquired. The transmission of unnecessary measurement data may be omitted in this way, to reduce an amount of data communication and to acquire the measurement data required for analysis in a short time.

The analysis unit 42 performs the analysis on the basis of the measurement data acquired by the acquisition unit 41, and acquires (or determines) a result of analyzing an eating situation of the user at the time of eating. According to examples, the analysis result includes attribute information indicating an attribute of food determined to have been chewed (ingested) by the user at the time of eating. The attribute of the food includes at least one of a size, a hardness, and a type of food. The type of food is, for example, information for specifying food such as almonds, rice, and strawberries. According to examples, the analysis result includes attribute information including all of a size, hardness, and type of food determined to have been chewed by the user, and an estimated value of an amount of chewing muscle activity of the user at the time of eating. The analysis results may include various types of information (for example, the number of times of chewing for each bite, occlusal force for each bite, and a posture for each bite such as a posture of a head at the time of eating) obtained by analyzing the measurement data using, for example, a statistical scheme, in addition to the above. Attribute information to be determined of the food may be information at least including a hardness. As will be further described below, a hardness attribute of a chewing target may be estimated through detection of an acceleration and/or an angular velocity of a movement of the lower jaw at the time of a first chewing operation (first chewing motion) and a second chewing operation (second chewing motion) of the chewing target. The first and second chewing operations correspond to first and second chewing motions (occlusal movements) during the chewing of the bite of food. Accordingly, the hardness of the chewing target can be estimated, so as to more easily provide a dietary habits improvement proposal (or dietary habits recommendation), including recommending ingestion of harder food.

The analysis unit 42 acquires a part or all of the above analysis result from the measurement data by using an analysis model (an analysis model M1) stored in the analysis model storage unit 43. According to examples, the analysis unit 42 extracts (acquires) chewing information (time-series data D1 and D2 illustrated in FIGS. 7 and 8) that is time-series information indicating a jaw movement for one bite of food chewed by the user, from the measurement data. The analysis unit 42 inputs the chewing information for one bite to the analysis model, and acquires information output from the analysis model as a part of the analysis result. According to examples, the information output from the analysis model includes attribute information indicating the attribute of the food that the user is determined to have chewed according to the jaw movement for one bite (e.g., the size, hardness, and type of food), and the estimated value of the amount of chewing muscle activity for one bite. Examples of such an analysis model will be further described.

Here, the jaw movement for one bite corresponds to a jaw movement in a period from a time when the user opens his or her mouth to put food for one bite in an oral cavity and puts the food in the mouth to a time when the user opens the mouth again to put the next food in the oral cavity. Alternatively, since the user usually opens the mouth to put the food for one bite in the oral cavity, puts the food in the mouth, chews the food, swallows the food, and then opens the mouth again to put the next food in the oral cavity, the jaw movement for one bite may be a jaw movement in a period from a time when the user opens the mouth to put the food for one bite in the oral cavity to a time when the chewing ends. That is, the jaw movement for one bite corresponds to a jaw movement during a period in which food for one bite is put in the oral cavity and then chewed without adding more food into the oral cavity. The jaw movement for one bite may be considered as a jaw movement in a period at least including a period from start to end of chewing the food for one bite put in the oral cavity between opening the mouth to chew the food for one bite and opening the mouth to chew the next food during a meal. Such a meal can be defined as described above because the chewing of food for one bite is usually repeated a plurality of times. It may be determined that the chewing ends when a certain period has elapsed in a state in which there is no jaw movement after the chewing ends, so that information on a last jaw movement for one bite can be processed. Further, the jaw movement for one bite may be considered as a jaw movement in a chewing period from opening the mouth to chew food for one bite to swallowing the food for one bite put in the oral cavity without adding more food in the mouth.

The generation unit 44 generates proposal information (or recommendation information) related to eating for the user on the basis of the analysis result acquired by the analysis unit 42. Examples of the proposal information include advice on meal content (for example, calling attention such as "the number of times of chewing is low" and "the user does not eat rice"), evaluation of a recent meal trend (an evaluation compared with standard dietary habits), and advice for improving dietary habits (for example, positive proposals such as: it is recommended to increase the number of times of chewing; it is recommended to keep a meal time constant; and it is recommended to increase a frequency at which the user ingests hard food because the user has recently not eaten hard food). The proposal information may be, for example, one template that is selected from a plurality of templates prepared in advance (for example, data including text according to content of a proposal or recommendation), or may be a combination of several templates (that is, complex proposal content), depending on examples. The advice for meal content or the advice for improving the dietary habits may be an eating behavior improvement proposal (a direct eating behavior improvement proposal) for directly proposing a better eating behavior to the user. Since the evaluation of the recent trend of eating also has an effect of motivating the user for improvement of the evaluation when the evaluation is unfavorable, the evaluation may be an eating behavior improvement proposal for indirectly encouraging the user to improve eating behavior (an indirect eating behavior improvement proposal).

The generation unit 44 generates (acquires) a part or all of the proposal information from a part or all of the analysis result acquired by the analysis unit 42 by using the proposal model (proposal model M2) stored in the proposal model storage unit 45. As an example, the generation unit 44 inputs the analysis result corresponding to a predetermined period to the proposal model, and acquires information output from the proposal model as a part of the proposal information described above. Here, the predetermined period is, for example, a meal period for one meal, or a meal period for one day (that is, a period including breakfast, lunch, snack, and dimmer). Examples of such a proposal model will be described further below.

The output unit 46 outputs the proposal information generated by the generation unit 44. According to examples, the output unit 46 outputs the proposal information to the display unit 47. For example, the output unit 46 generates display data for displaying content of the proposal information on the screen, and outputs the display data to the display unit 47.

The display unit 47 displays the proposal information. The display unit 47 is provided by, for example, a display device included in the user terminal 4. The display unit 47 presents the content of the proposal information to the user by displaying the display data acquired from the output unit 46. This makes it possible for the user to confirm proposal content according to an analysis result for the measurement data acquired by the sensor 20 of the denture 2.

Hereinafter, an example of a structural configuration of the acquisition unit 41, the analysis unit 42, an analysis model training data storage unit 52, the analysis model storage unit 43, the generation unit 44, and the output unit 46 will be described. The acquisition unit 41 includes an interface that acquires the measurement data. When the measurement data is processed, the acquisition unit 41 includes an interface and a circuit. The circuit may be included in a processor. The analysis unit 42 includes a program for performing the analysis, and a circuit that executes the program. The circuit may be included in a processor. The program for performing the analysis is stored in memory, for example, in the form of processor-readable data and instructions. The analysis model training data storage unit 52 includes a memory. The analysis model storage unit 43 includes a memory. The generation unit 44 includes a program for performing the generation, and a circuit that executes the program. The circuit may be included in a processor. The program for performing the generation is stored in memory, for example, in the form of processor-readable data and instructions. The output unit 46 includes a program for performing an output, and a circuit that executes the program. The circuit may be included in a processor. The program for performing the output is stored in memory, for example, in the form of processor-readable data and instructions.

Configuration of Server

As illustrated in FIG. 1, the server 5 includes an analysis model training data generation unit 51, an analysis model training data storage unit 52, and an analysis model learning unit 53 as functional elements for generating the analysis model described above. Further, the server 5 includes a proposal model training data generation unit 54, a proposal model training data storage unit 55, and a proposal model learning unit 56 as functional elements for generating the above-described proposal model (or recommendation model). The server 5 is a computer device including a processor (for example, a CPU) and a memory (for example, a ROM and a RAM). The server 5 may be provided by, for example, one or more devices operating as a cloud server.

The analysis model training data generation unit 51 generates training data for learning of the analysis model. The analysis model training data storage unit 52 stores the training data generated by the analysis model training data generation unit 51. The analysis model learning unit 53 generates an analysis model, which is a learned model, by executing machine learning using the training data stored in the analysis model training data storage unit 52.

Figure 3:
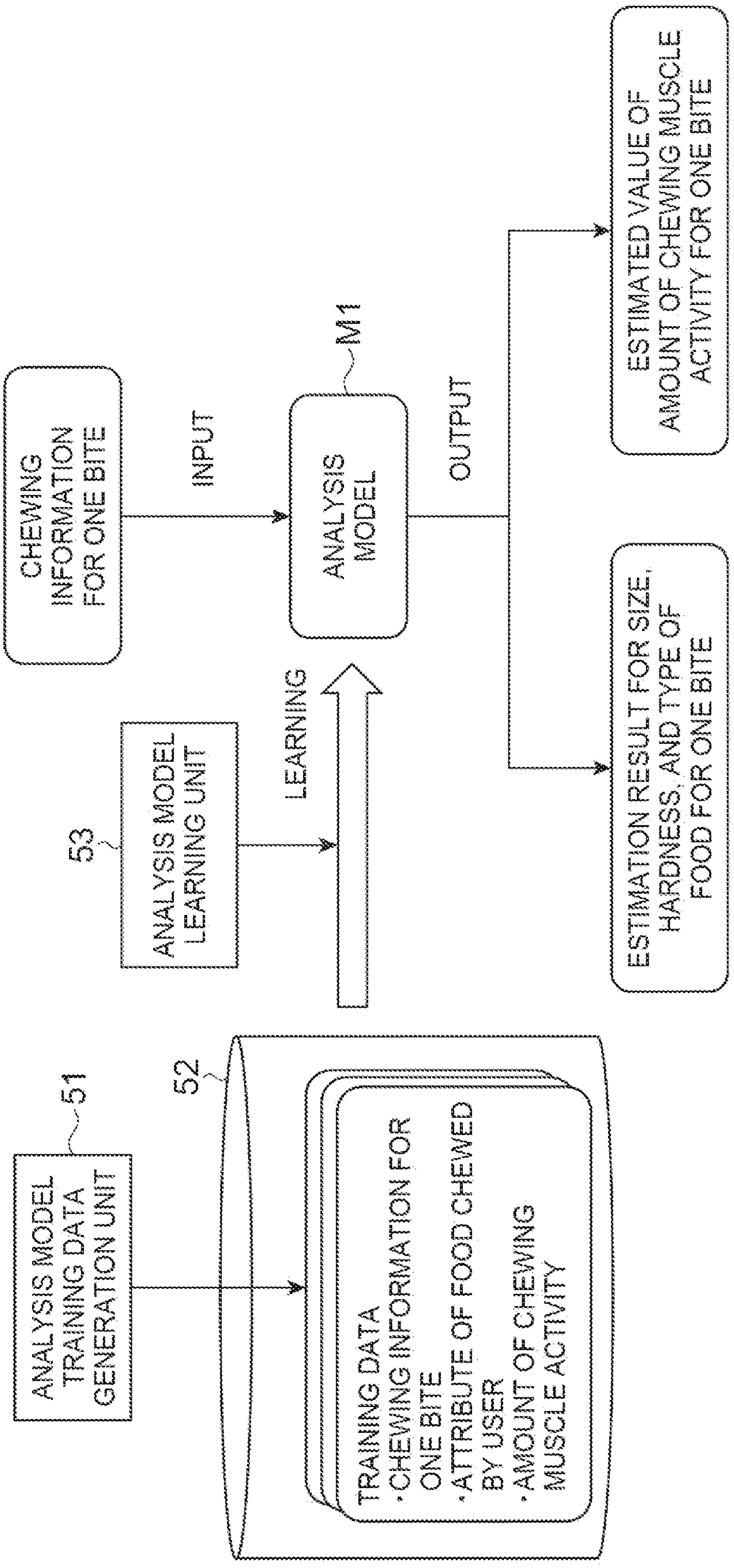
FIG. 3 is a schematic diagram illustrating an overview of an analysis model.

FIG. 3 is a diagram schematically illustrating an overview of the analysis model. As illustrated in FIG. 3, first, the analysis model training data generation unit 51 generates a plurality of sets of training data including chewing information (first information), which is time-series information indicating a past jaw movement for one bite acquired for the user, and information on actual meal content of the user corresponding to the past jaw movement for one bite. The information on the actual meal content of the user is information including an attribute (second information) of the food actually chewed according to the past jaw movement for one bite by the user. According to examples, the amount of chewing muscle activity corresponding to the past jaw movement for one bite is also included as the information on the actual meal content. This amount of chewing muscle activity is measured at the time of actual meal of the user. The information on the actual meal content may include results of measuring occlusal force, a posture of a head, and the like at the time of an eating operation, in addition to the above.

Such training data can be obtained, for example, by associating chewing information for each bite extracted from measurement data when the user is caused to eat various foods with the actual meal content of the user. However, a method of acquiring training data is not limited to the above. The training data may be acquired, for example, by causing the user to wear smart glasses capable of recording a video of a mouth of the user and logging an actual meal state of the user with the smart glasses. For example, chewing information for each bite during a meal is acquired from the measurement data acquired by the sensor 20 of the denture 2, and the actual meal content of the user is ascertained from the video acquired by the smart glasses. It is possible to obtain the above-described training data by associating the actual meal content of the user ascertained from the video acquired by the smart glasses with the chewing information for each bite. The training data generated in this way is stored in the analysis model training data storage unit 52.

Subsequently, the analysis model learning unit 53 generates the analysis model M1 that is a learned model, by executing machine learning using the training data stored in the analysis model training data storage unit 52. A scheme of the machine learning executed by the analysis model learning unit 53 is not limited to a specific scheme and, for example, various schemes such as a support vector machine (SVM), a neural network, and deep learning can be used. For example, when the analysis model M1 is provided by the neural network, a learned model in which parameters of an intermediate layer of the neural network are tuned by the training data is obtained as the analysis model M1.

Such an analysis model M1 obtained by machine learning is a learned model configured to receive the chewing information for one bite of food chewed by the user and output an estimation or assessment result for meal content of the user corresponding to the chewing information for one bite. Here, the assessment result for the meal content of the user includes an assessment result for the attribute of the food such as the size, hardness, and type of food for one bite, and the estimated value of the amount of chewing muscle activity for one bite. The analysis model M1 generated by the analysis model learning unit 53 is provided from the server 5 to the user terminal 4 and stored in the analysis model storage unit 43 of the user terminal 4.

The proposal model training data generation unit 54 generates training data for learning of the proposal model. The proposal model training data storage unit 55 stores the training data generated by the proposal model training data generation unit 54. The proposal model learning unit 56 generates a proposal model, which is a learned model, by executing machine learning using the training data stored in the proposal model training data storage unit 55.

Figure 4:
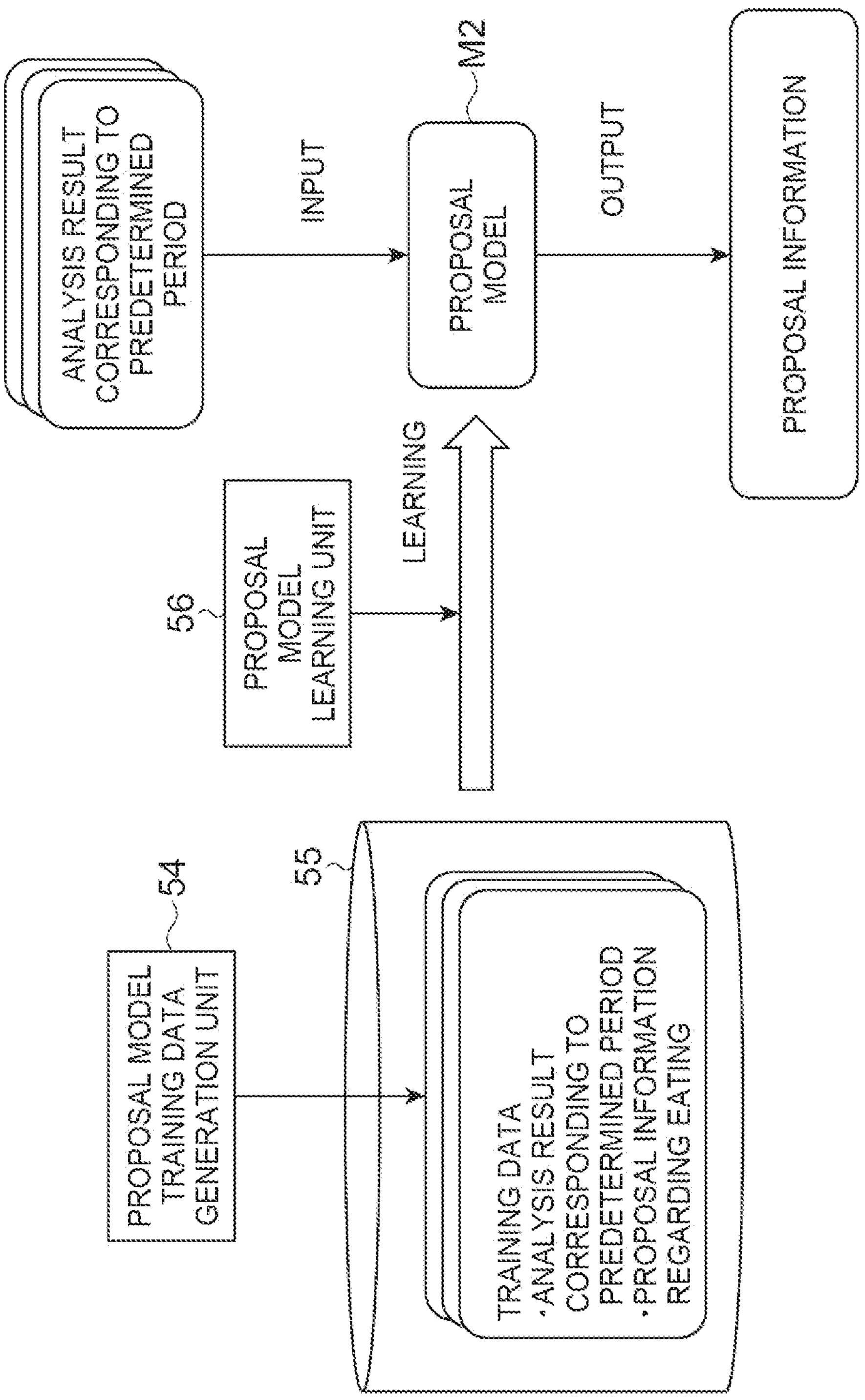
FIG. 4 is a schematic diagram illustrating an overview of a proposal model.

FIG. 4 is a diagram schematically illustrating an overview of the proposal model (or recommendation model). As illustrated in FIG. 4, first, the proposal model training data generation unit 54 generate a plurality of sets of training data including an analysis result corresponding to a past predetermined period acquired for the user, and proposal information regarding eating according to the analysis result. Here, as an example, the predetermined period is a meal period for one meal (for example, breakfast). Further, the analysis result corresponding to the predetermined period may include, for example, attribute information (the size, hardness, and type) of the food chewed by the user in the predetermined period, the amount of chewing muscle activity in the predetermined period, the total number of times of chewing in the predetermined period, occlusal force in a predetermined period, the posture of the head in the eating operation in the predetermined period. The occlusal force may be actually measured, but may be analyzed from a standard average value based on, for example, sex, age, physique, and the like. That is, the analysis result corresponding to the predetermined period input to the proposal model may include not only information obtained by using the above-described analysis model M1 (e.g., attribute information of food estimated or determined to have been chewed by the user, the estimated value of the amount of chewing muscle activity, and the like), but also information obtained by using a statistical scheme or the like without using the analysis model M1. The posture of the head may be measured on the basis of a detection result of the sensor unit 21.

The proposal information regarding eating included in the training data may be the eating behavior improvement proposal described above. Alternatively, the proposal information may be, for example, proposal information according to a health condition (for example, cold, stomachache, or headache) of the user in the past predetermined period. The training data generated by the proposal model training data generation unit 54 is stored in the proposal model training data storage unit 55. It is conceivable that the health condition of the user is reflected in the eating operation (e.g., chewing movement) of the user. Although there may be individual differences in users, for example, when a user suffers from the cold, stomachache, or the like, a meal amount is likely to be less than usual, food to be ingested is likely to be biased, or occlusal force is likely to be less than usual. Further, when the user suffers from the headache, the posture of the head is also likely to be worse than usual (for example, slanted). Thus, it can be said that there is a certain correlation between the health condition of the user and the eating operation of the user, such that there is also a certain correlation between proposal information according to the health condition of the user (that is, proposal information considered to be useful for the user on the basis of the health condition of the user) and the eating operation of the user. Therefore, according to the machine learning based on the training data described above, it is possible to generate a proposal model configured to receive the analysis result corresponding to the predetermined period and output the proposal information according to the health condition of the user assessed from the analysis result. Examples of the proposal may include a proposal regarding healing support, such as presenting a cause of a disease to the user and making an appropriate menu proposal when the disease is suspected, and performing recommendation for consultation. The recommendation for consultation, or the like is a proposal (soundness proposal) for improving the health condition of the user in connection with eating.

Subsequently, the proposal model learning unit 56 generates the proposal model M2, which is a learned model, by executing machine learning using the training data stored in the proposal model training data storage unit 55. A scheme of the machine learning executed by the proposal model learning unit 56 is not limited to a specific scheme and, for example, various schemes such as SVM, a neural network, and deep learning can be used. For example, when the proposal model M2 is provided by the neural network, a learned model in which parameters of an intermediate layer of the neural network are tuned by the training data is obtained as the proposal model M2.

Such a proposal model M2 obtained by machine learning is a learned model configured to receive the analysis result corresponding to the predetermined period of the user and output the proposal information corresponding to the analysis result. The proposal model M2 generated by the proposal model learning unit 56 is provided from the server 5 to the user terminal 4, and is stored in the proposal model storage unit 45 of the user terminal 4.

Hereinafter, an example of a structural configuration of the analysis model training data generation unit 51, the analysis model learning unit 53, the proposal model training data generation unit 54, the proposal model training data storage unit 55, and the proposal model learning unit 56 will be described. The analysis model training data generation unit 51 includes a program for generating training data for an analysis model, and a circuit that executes the program. The circuit may be included in a processor. The program for generating the training data for an analysis model is stored in memory, in the form of processor-readable data and instructions. The analysis model learning unit 53 includes a program for performing analysis model learning, and a circuit that executes the program. The circuit may be included in a processor. The program for performing the analysis model learning is stored in memory, for example, in the form of processor-readable data and instructions. The proposal model training data generation unit 54 includes a program for performing generation of training data for a proposal model, and a circuit that executes the program. The circuit may be included in a processor. The program for generating the training data for a proposal model is stored in memory, for example, in the form of processor-readable data and instructions. The proposal model training data storage unit 55 includes a memory. The proposal model learning unit 56 includes a program for performing proposal model learning, and a circuit that executes the program. The circuit may be included in a processor. The program for performing the proposal model learning is stored in memory, for example, in the form of processor-readable data and instructions.

Processing of Analysis Unit and Generation Unit

Figure 5:
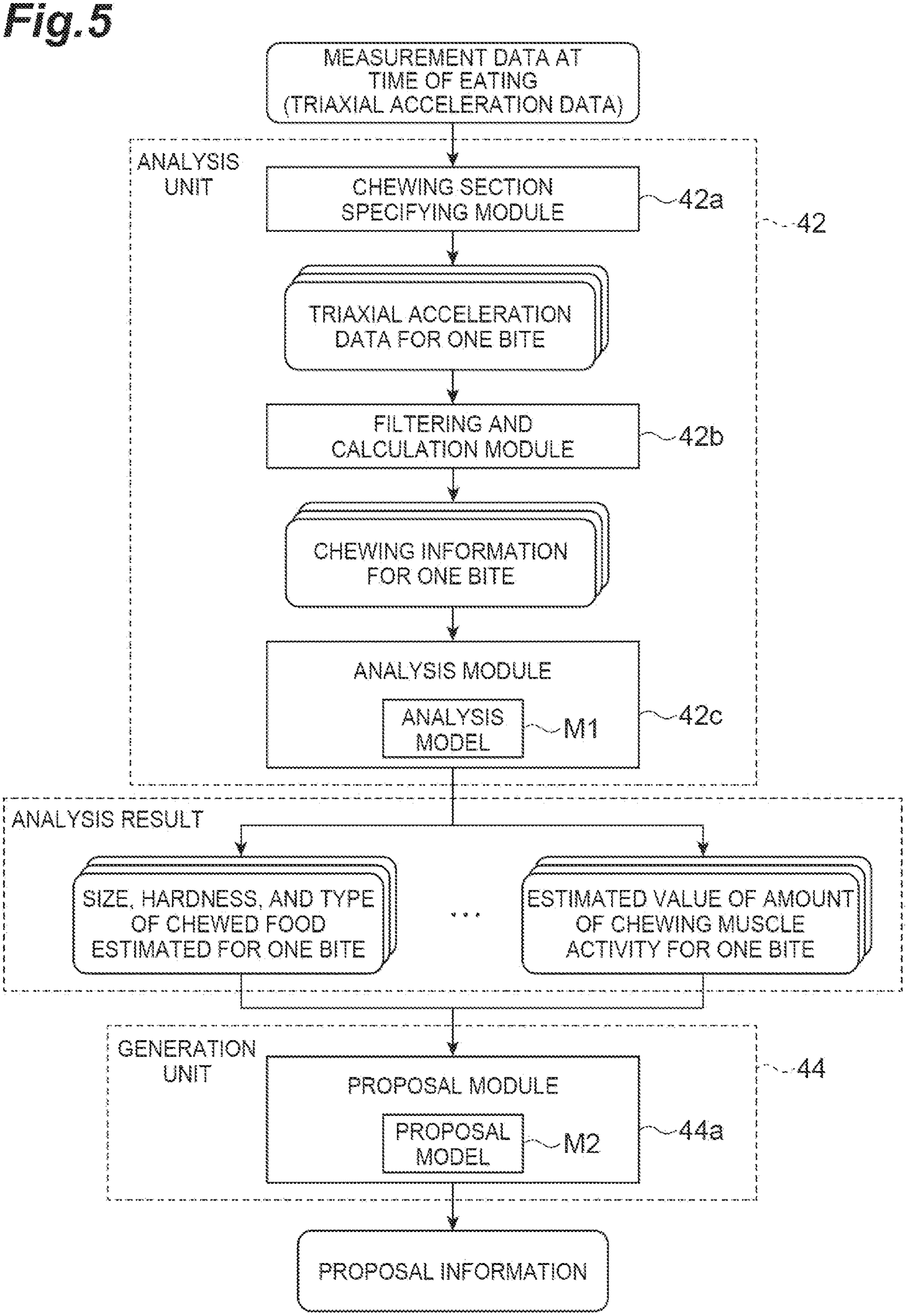
FIG. 5 is a flow chart illustrating an example processing carried out by an analysis unit and a generation unit.

An example of processing of the analysis unit 42 and the generation unit 44 will be described with reference to FIGS. 5 to 8. FIG. 5 is a diagram illustrating an example of a processing flow until the generation of the proposal information from the measurement data at the time of eating (the measurement data acquired by the acquisition unit 41). As illustrated in FIG. 5, the analysis unit 42 may include a chewing section specifying module 42*a*, a filtering and calculation module 42*b*, and an analysis module 42*c*. Further, the generation unit 44 includes a proposal module 44*a*. These modules are provided by, for example, programs for executing various processing. In FIG. 5, the analysis model M1 is shown in the analysis module 42*c*. This shows a configuration in which the analysis module 42*c* uses the analysis model M1 in some form, such as a case in which the analysis model M1 is stored in a memory of the analysis module 42*c*, a case in which the analysis module 42*c* accesses the analysis model M1 in the analysis model storage unit 43, or a case in which the analysis model M1 is taken into the memory of the analysis module 42*c* from the analysis model storage unit 43.

Chewing Section Specifying Module

First, the analysis unit 42 extracts the triaxial acceleration data for each bite from measurement data (here, triaxial acceleration data) for a certain time period (for example, for one day from a time when the user wears the denture 2 after waking up to a time when the user removes the denture 2 before going to bed), using the chewing section specifying module 42*a*. A period from the mounting of the denture 2 to the removal of the denture 2 in the daily life of the user may be referred to as a denture mounting period. According to examples, the chewing section specifying module 42*a* specifies (or identifies) a chewing section for each bite included in the measurement data (that is, a section in which the user puts food for each bite in the mouth and performs a chewing operation). A plurality of chewing operations for crushing food in the oral cavity is included in the chewing section for each bite. The chewing section specifying module 42*a* extracts measurement data corresponding to each specified chewing section as data for one bite.

Figure 6:
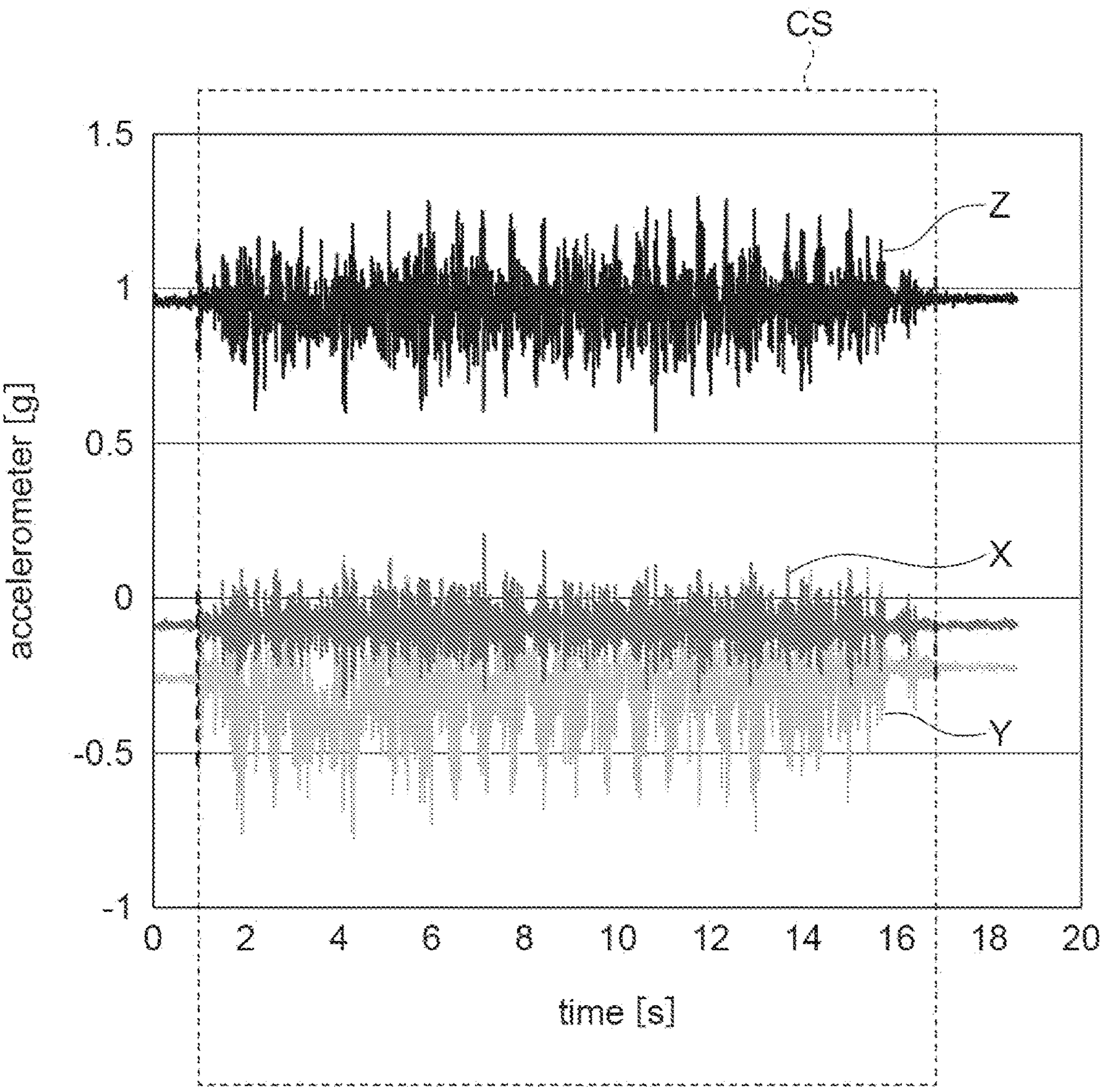
FIG. 6 is a graph illustrating an example of a chewing section that is identified by a chewing section specifying module.

FIG. 6 is a diagram illustrating an example of a chewing section CS that is identified by the chewing section specifying module 42*a*. In FIG. 6, X, Y, and Z indicate accelerations in an X-axial direction, a Y-axial direction, and a Z-axial direction, respectively. Here, it is known that a pattern of a jaw movement at the time of chewing of a certain user is substantially constant regardless of a type of food, or the like. By using this, the chewing section specifying module 42*a* may identify the chewing section as follows, according to an example.

First, the chewing section specifying module 42*a* acquires a cycle of the jaw movement at the time of chewing of the user (hereinafter referred to as a "jaw movement cycle") in advance. For example, the jaw movement cycle can be acquired (calculated) on the basis of advance preliminary measurement (for example, video observation of the chewing movement of the user). Further, for example, when a section in which it is proven that the user performs a chewing operation is present in the measurement data, it is possible to acquire a cycle of the movement component as the jaw movement cycle by extracting a periodic movement component observed in the section. In the jaw movement cycle, a maintenance operation in which the jaw is not moved may be included, in addition to an operation of actually moving the jaw. Hereinafter, in the jaw movement cycle, the operation of moving the jaw is referred to as an active jaw movement, and the maintenance operation in which the jaw is not moved is referred to as a passive jaw movement. Aperiodic jaw movement may be the active jaw movements or may be a combination of the active jaw movement and the passive jaw movement. Therefore, the jaw movement for one bite described above may be the active jaw movement or may be a combination of the active jaw movement and the passive jaw movement.

Subsequently, the chewing section specifying module 42*a* identifies a section in which a periodic movement component is observed at a cycle coinciding with or similar to the jaw movement cycle from the measurement data, as the chewing section. For example, when the chewing section specifying module 42*a* detects a section in which the periodic movement component lasts for a predetermined threshold time (for example, several seconds) or more, the chewing section specifying module 42*a* identifies the detected section as the chewing section. The measurement data corresponding to the chewing section identified in this way is extracted as the data for each bite. By such processing of the chewing section specifying module 42*a*, the chewing section CS is identified from the measurement data (here, triaxial acceleration data), as illustrated in FIG. 6. Thus, a chewing section CS for each bite is identified for each meal period of the user (for example, a period such as breakfast, lunch, snack, dimmer) included in the measurement data. That is, a plurality of chewing sections CS are identified for each meal period included in the measurement data. The measurement data included in each chewing section CS is extracted as the triaxial acceleration data for each bite. The chewing section specifying module 42*a* may extract a jaw movement for chewing from jaw movements of the user and determine a start time of chewing. Further, the chewing section specifying module 42*a* may determine that the chewing ends when a certain time has elapsed in a state in which there is no jaw movement after the chewing ends. The chewing section specifying module 42*a* may identify the chewing section CS in a meal section by separating start and end of one meal and setting a section of the one meal as the meal section.

Filtering and Calculation Module

Next, the analysis unit 42 removes an influence of a noise component and a gravitational acceleration included in the triaxial acceleration data for one bite using the filtering and calculation module 42*b*. According to examples, the filtering and calculation module 42*b* performs noise removal on high-frequency components included in the triaxial acceleration data for one bite using, for example, a low-pass filter, and performs offset correction on the triaxial acceleration data for one bite. The offset correction is processing of removing a signal component due to the gravitational acceleration acquired by the acceleration sensor. Processing of removing or reducing a noise component that may adversely affect the analysis in this way may be referred to as "adverse component countering processing". The filtering and calculation module 42*b* may be referred to as an "adverse component countering module" that performs the adverse component countering processing.

Figure 7:
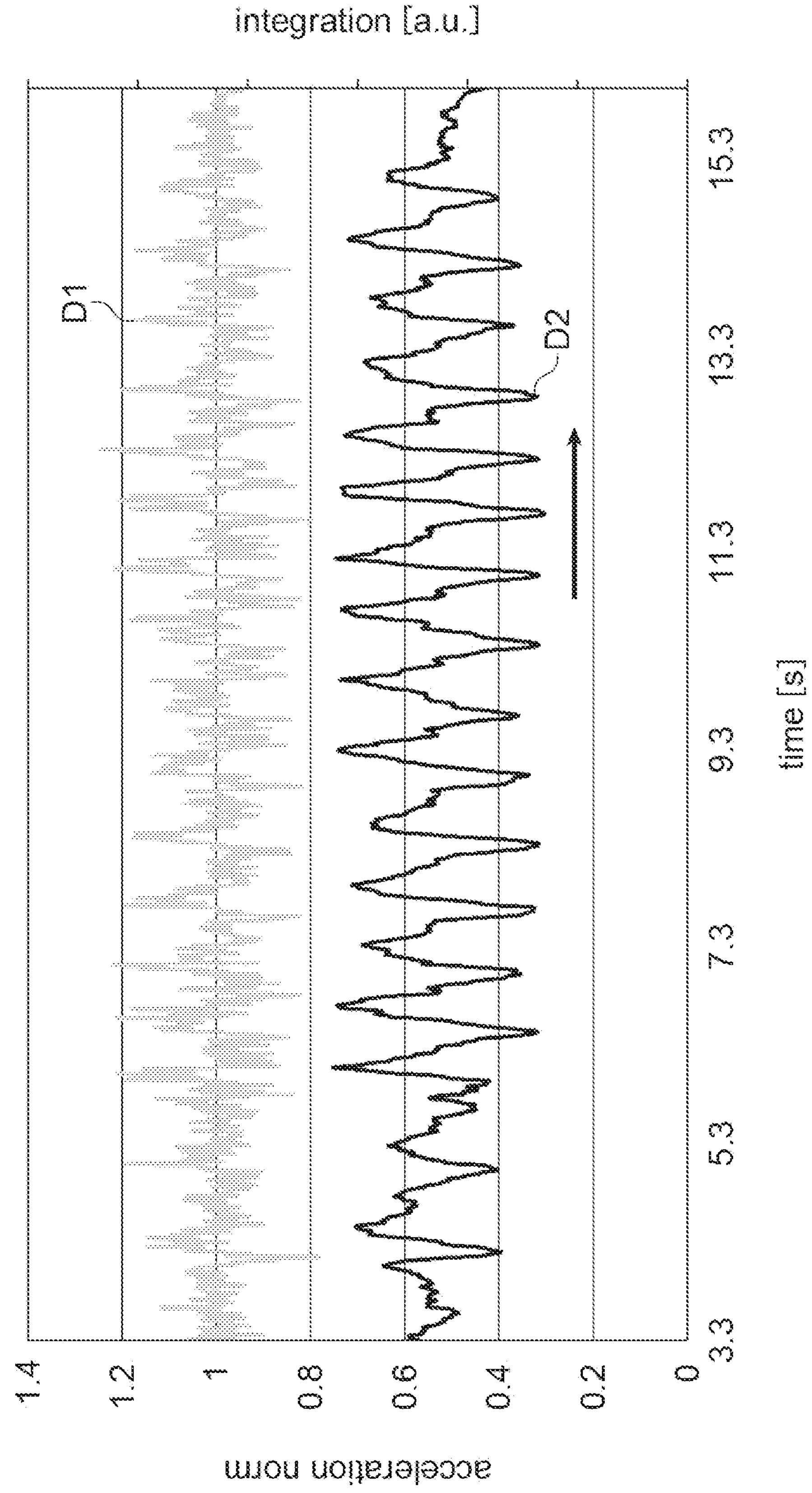
FIG. 7 is a graph illustrating an example of chewing information representing a jaw movement for chewing a bite of food.

As illustrated in FIG. 7, the filtering and calculation module 42*b* acquires the time-series data D1 indicating a norm of acceleration on the basis of the triaxial acceleration data for one bite after the noise removal and the offset correction. Subsequently, the filtering and calculation module 42*b* subtracts a gravitational acceleration (1*g*) from the norm of the acceleration, and performs integral on a subtraction result. Accordingly, time-series data D2 is obtained. The time-series data D2 is waveform data similar to the jaw movement of the user (an angular velocity of the lower jaw).

The time-series data D1 and D2 are used as the chewing information for one bite that is input to the analysis model M1. That is, the analysis unit 42 extracts the time-series data D1 and D2 that is the chewing information indicating the jaw movement for one bite of food chewed by the user from the measurement data acquired by the acquisition unit 41 using the chewing section specifying module 42*a* and the filtering and calculation module 42*b* described above. As described above, the chewing information (the time-series data D1 and D2) is extracted for each chewing section CS specified by the chewing section specifying module 42*a*.

It is possible to ascertain information on a size of an opening of the user (that is, a size of opening of the lower jaw with respect to the upper jaw to chew food) and an occlusal movement (chewing operation) from the time-series data D1 and D2. For example, it is possible to extract a section until the user opens the mouth again widely to insert the bite of food into the mouth after closing the mouth, chewing the food, and swallowing the food in a state in which the user opens the mouth widely (that is, a state in which the lower jaw is separated from the upper jaw), from characteristics of waveforms of the time-series data D1 and D2. The section is a section in which one chewing operation (e.g., an operation of opening the mouth once, chewing food, and then opening the mouth again for the next chewing operation) is performed.

Figure 8:
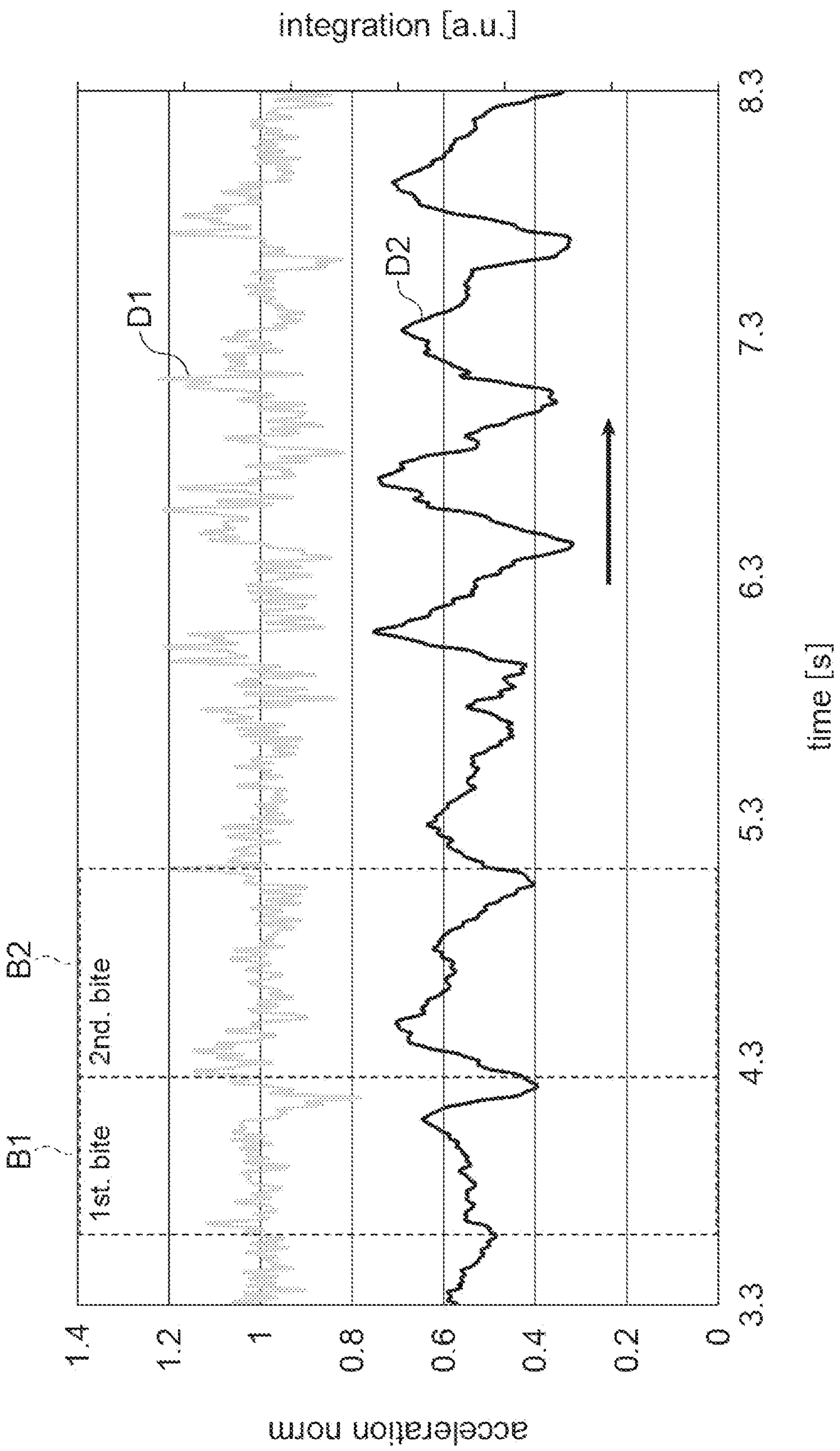
FIG. 8 is a graph illustrating an example of chewing information including sections corresponding to a first chewing motion and a second chewing motion.

FIG. 8 is a diagram illustrating a section B1 corresponding to a first chewing operation and a section B2 corresponding to a second chewing operation extracted from the time-series data D1 and D2. An occlusal movement of the first chewing operation (data in the section B1) and an occlusal movement of the second chewing operation (data in the section B2) of a bite are portions that are particularly closely related to a type of food (a chewing material) (a type of food specified from hardness, cohesiveness, or the like), a size of the food, and the amount of chewing muscle activity. That is, the data in the sections B1 and B2 are portions that are particularly indicative of characteristics according to the type of food, the size of the food, and the amount of chewing muscle activity.

FIG. 9 illustrates an example of data obtained by the sensor 20 of the denture 2 by mounting the denture 2 on a robot simulating an actual jaw movement at the time of chewing of a person. Here, the sensor unit 21 of the sensor 20 includes an angular velocity sensor that detects an angular velocity of a rotational motion of the lower jaw around an axis connecting a reference point of the lower jaw, in addition to the acceleration sensors in the triaxial directions. An example of such an angular velocity sensor may include an angular velocity sensor that detects an angular velocity of a rotational motion of the lower jaw around an axis connecting kinetic condyle points of left and right lower jaw condyles of the lower jaw. As the angular velocity sensor, angular velocity sensors in triaxial directions may be used. When a robot is used, it may be easier to set a reference point among the points. Time-series data D3 is data obtained by performing integral on a norm of the angular velocity obtained from the data acquired by angular velocity sensors in the triaxial directions. That is, the time-series data D3 is data corresponding to an angle of the lower jaw with respect to the upper jaw at each point in time. Time-series data D4 is data corresponding to the time-series data D2 described above (that is, data obtained by performing integral on a result of subtracting the gravitational acceleration from the norm of acceleration). In a graph illustrated in FIG. 9, when a value of the time-series data D3 is less (on a lower side), an opening of the mouth (the opening of the lower jaw with respect to the upper jaw) is wider. Although the analysis unit 42 acquires the chewing information (here, the time-series data D1 and D2) for one bite only from the triaxial acceleration data in the examples of FIGS. 5 to 8, the analysis unit 42 may acquire data corresponding to the time-series data D3 as chewing information for one bite when the sensor unit 21 includes angular velocity sensors in triaxial directions.

Figure 9A:
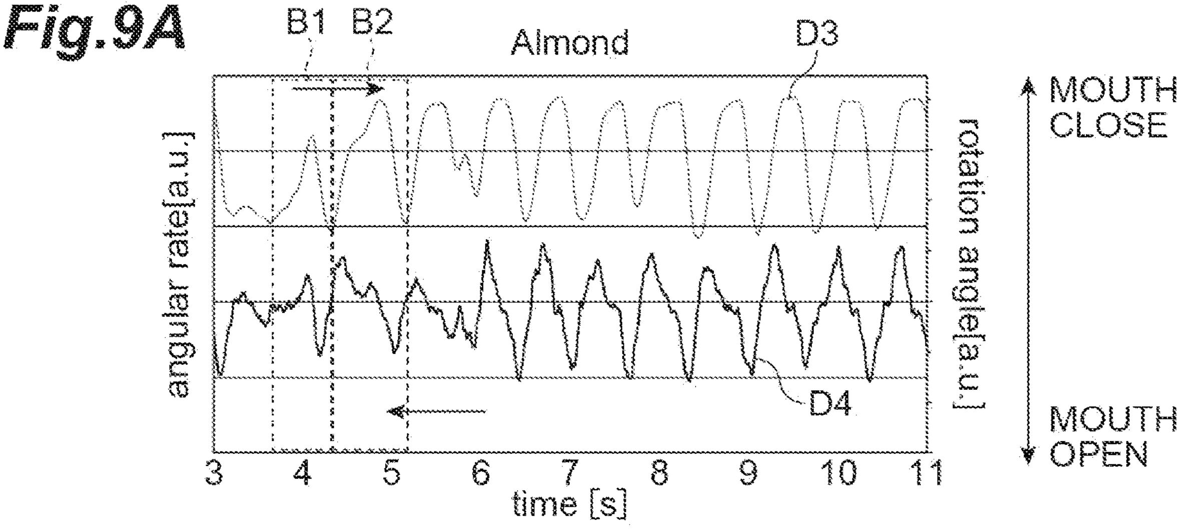
FIG. 9A is a graph showing a simulation result when almonds are chewed.
Figure 9B:
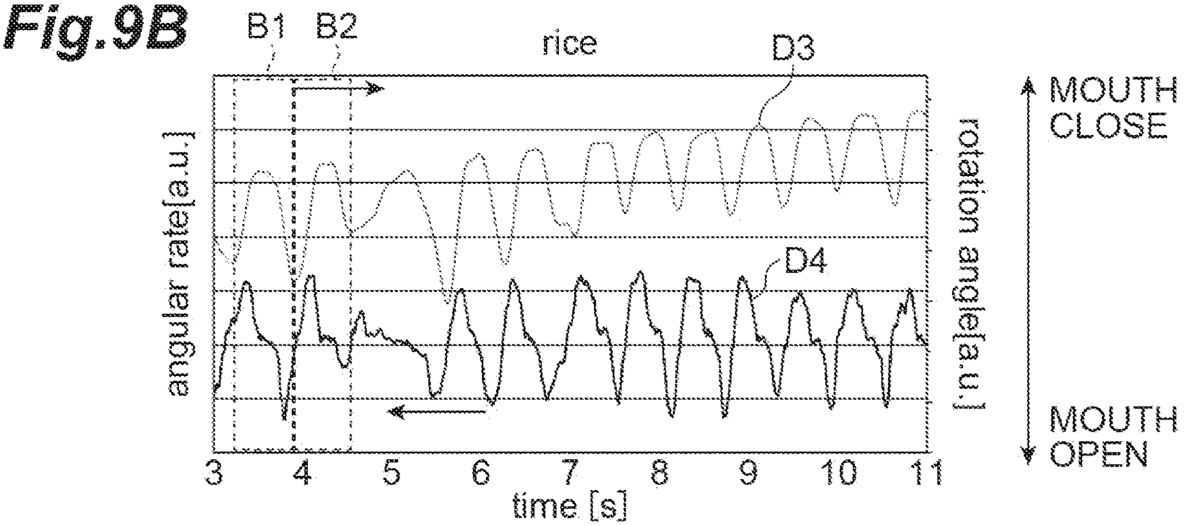
FIG. 9B is a graph showing a simulation result when rice is chewed.
Figure 9C:
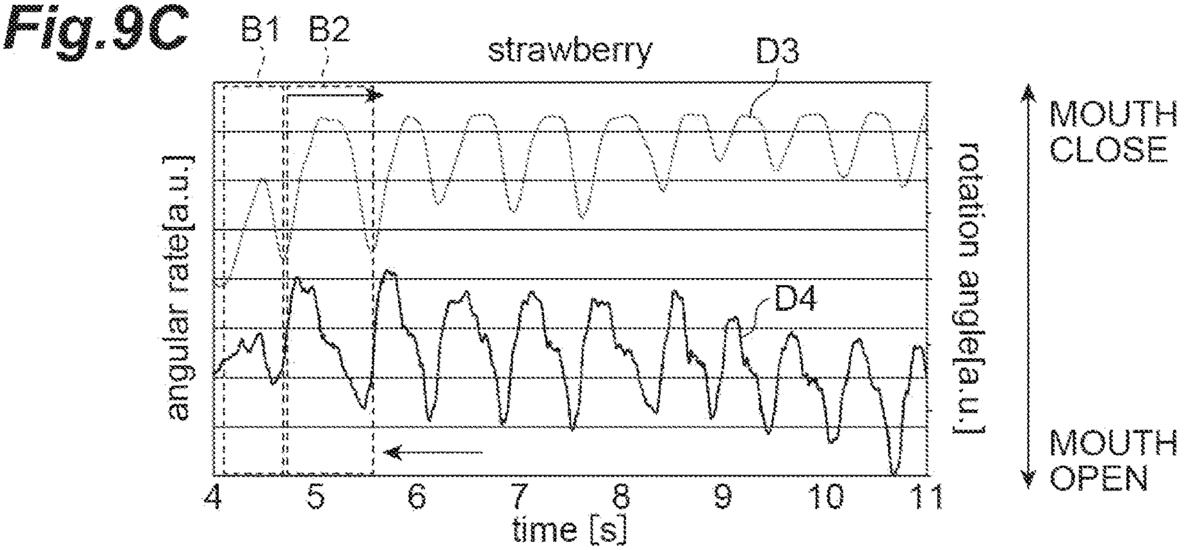
FIG. 9C is a graph showing a simulation result when strawberries are chewed.

FIG. 9A is a graph showing a simulation result when almonds are chewed. FIG. 9B is a graph showing a simulation result when rice for one bite is chewed. FIG. 9C is a graph showing a simulation result when strawberries are chewed. Here, physical characteristics of each food are as follows.

Almonds: Relatively small size and relatively hard.

Rice: Relatively small size and relatively soft.

Strawberries: Relatively large size and relatively soft.

As illustrated in FIGS. 9A-9C, in an overall waveform of the time-series data D3 and D4, a difference between foods (that is, a difference according to a difference in the physical characteristics) appears. In particular, in the time-series data D3 and D4, the difference between foods appears more noticeably in portions corresponding to a first chewing operation (the section B1) and a second chewing operation (the section B2). For example, in the second chewing operation for the almonds, characteristics of a further chewing operation appears after the jaw movement has stopped. Further, for rice with high adhesiveness, the number of times of chewing (the number of chewing operations) per unit time is greater than those of the almonds and the strawberries. Further, for strawberries, the size of the opening in the second and subsequent chewing operations is relatively small. It is estimated that this is because a bolus is eaten while a tongue is moved.

Thus, it can be seen that characteristics according to physical characteristics of a food to be chewed appear in the chewing information for one bite of the food chewed by the user. Although there may be individual differences in the jaw movement at the time of chewing, it is possible to obtain the analysis model M1 according to characteristics of the jaw movement at the time of chewing, that is particular to the user by causing the analysis model M1 to be learned using a plurality of pieces of training data (correct answer data) obtained from the past meal of the user, as described above.

The input data for the analysis model M1 includes time-series information (first chewing information) indicating a jaw movement corresponding to a first chewing operation and time-series information (second chewing information) indicating a jaw movement corresponding to a second chewing operation. The first chewing information is data included in the section B1, and the second chewing information is data included in the section B2. That is, the data included in the section B1 may be explicitly input to the analysis model M1 as data corresponding to the first chewing operation, and the data included in the section B2 may be explicitly input to the analysis model M1 as data corresponding to the second chewing operation. In this case, the above-described analysis model training data generation unit 51 may extract data corresponding to the first chewing operation (that is, information corresponding to the first chewing information) and the data corresponding to the second chewing operation (that is, information corresponding to the second chewing information) from the past chewing information for one bite acquired for the user, and include these pieces of extracted data in the training data for an analysis model. Thus, the training data may at least include the data corresponding to the first chewing operation and the data corresponding to the second chewing operation. In this case, the analysis model M1 is learned to output analysis results for the first chewing information and the second chewing information (for example, the attribute information of the food determined to have been chewed by the user, and the estimated value of the amount of chewing muscle activity for one bite). The data corresponding to the first chewing operation may be referred to as "first chewing information analysis education data", and the data corresponding to the second chewing operation may be referred to as "second chewing information analysis education data".

Analysis Module

Then, the analysis unit 42 acquires the above-described analysis result from the chewing information for one bite using the analysis module 42*c*. The analysis unit 42 inputs the chewing information for one bite to the analysis model M1 stored in the analysis model storage unit 43. As described above, only the time-series data D1 and D2 in the chewing section CS (hereinafter referred to as "entire section data") may be included in the chewing information for one bite input to the analysis model M1, only the time-series data D1 and D2 included in the sections B1 and B2 in the chewing section CS (hereinafter referred to as "specific section data") may be included in the chewing information for one bite, or both the entire section data and the specific section data may be included in the chewing information for one bite. In some examples, only one of the time-series data D1 and D2 may be included in the chewing information for one bite input to the analysis model M1. Further, when the time-series data corresponding to the time-series data D3 (that is, data indicating the angle of the lower jaw) described above is included in the chewing information for one bite as described above, the time-series data may be included in the chewing information for one bite that is input to the analysis model M1. A reason for paying of particular attention to the first chewing operation and the second chewing operation is that the first chewing operation and the second chewing operation show noticeable characteristics of the chewing target, however a chewing operation up to any plurality of times (n-th time) may be observed. That is, chewing information corresponding to first to n-th chewing operations may be used as the input data for the analysis model M1. The n times are set to the number of times less than a total number of chewing operations in the chewing section CS.

The analysis unit 42 acquires an attribute of the food (e.g., a size, hardness, or type of food) that is determined to have been chewed according to the jaw movement for one bite by the user, which is output from the analysis model M1, as the attribute information described above, using the analysis module 42*c*. That is, the analysis unit 42 (the analysis module 42*c*) executes assessment of the attribute using the analysis model M1. The attribute information of the food output from the analysis model M1 may be referred to as "determined attribute information", and an attribute of the food determined to be chewed may be referred to as a "determined attribute". Further, as described above, the analysis model M1 may output the estimated value of the amount of chewing muscle activity for one bite together with the attribute of the food. Further, the analysis model M1 may be configured to further output information additional to the above.

Further, the analysis unit 42 may acquire the information obtained without using the analysis model M1 as a part of the analysis result. The information obtained without using the analysis model M1 is, for example, information such as the occlusal force for each bite, and a posture for each bite (a posture of the head of the user at the time of the eating operation). Examples of a method of obtaining information without using the analysis model M1 include analyzing the measurement data by using a statistical scheme or the like, and using the sensor unit 21 to acquire the information.

For example, it is possible to derive the posture of the head of the user at the time of the eating operation from the triaxial acceleration data. For example, the analysis unit 42 derives a calculation equation for determining the posture (a direction of a face) of the head of the user from the triaxial acceleration data according to the following procedure in advance.

1. The denture 2 is caused to stand still to be directed to each of first, second, and third directions orthogonal to each other.
2. First acceleration data in the triaxial directions measured by the acceleration sensor of the sensor unit 21 when the denture 2 is caused to stand still to be directed to the first direction, second acceleration data in the triaxial directions measured by the acceleration sensor of the sensor unit 21 when the denture 2 is caused to stand still to be directed to the second direction, and third acceleration data in the triaxial directions measured by the acceleration sensor of the sensor unit 21 when the denture 2 is caused to stand still to be directed to the third direction are acquired.
3. A calculation equation for estimating (or determining) the posture of the head of the user is derived from the triaxial acceleration data corresponding to an arbitrary state in which the head of the user (including the lower jaw) is caused to stand still on the basis of a relationship between three directions (the first direction, the second direction, and the third direction) of the denture 2 and the triaxial acceleration data (the first acceleration data, the second acceleration data, and third acceleration data) corresponding to the respective directions.

The analysis unit 42 can estimate (calculate) the posture of the head of the user on the basis of the triaxial acceleration data in a state in which the user momentarily stands still (for example, at the time of occlusal in which the upper tooth and the lower tooth are engaged) in the time-series data D1 and D2, and the calculation equation.

The analysis unit 42 can acquire the analysis result corresponding to a predetermined period (e.g., a meal time for one meal) (e.g., information obtained by aggregating the analysis results corresponding to the respective chewing section CS included in the predetermined period) by using, for example, the analysis model M1 and/or the statistical scheme, as described above, for all pieces of chewing information included in the predetermined period.

Proposal Module

The generation unit 44 inputs a part or all of the analysis result corresponding to the predetermined period to the proposal model M2 using the proposal module 44*a*. Accordingly, the generation unit 44 acquires the information output from the proposal model M2 as the proposal information. Further, the generation unit 44 may acquire information such as an amount of one meal, nutritional balance, the number of times of chewing, meal time, and occlusal force by analyzing the analysis result corresponding to the predetermined period by using a statistical scheme or the like without using the proposal model M2, and generate the proposal information on the basis of the acquired information and a predetermined proposal generation rule. For example, the generation unit 44 may determine a targeted range of an amount of food for one meal (or a meal size) in advance, and generate proposal information for encouraging the amount of food to be in the range when the amount of food for one meal (an estimated value) obtained from the analysis result is outside the range. For example, when the amount of food (the estimated value) is less than the range, the generation unit 44 may extract text data "let's increase a meal size a little more" from template information prepared in advance, and generate the text data as the proposal information. The above-described proposal generation rule is information in which such a rule is defined in advance. The proposal information may be voice data. For example, when a sound generator such as a speaker is provided as the output unit 46, the proposal information may be output as voice data.

Further, the proposal information generated by the generation unit 44 may include various types of information considered to be useful for the user, such as information ascertained through, for example, statistical processing for the analysis result, a history of past meals of the user (information ascertained from the analysis result), in addition to the information with the content described above. Table 1 below shows an example of the proposal information (display items) generated by the generation unit 44.

TABLE 1

| Item No. | Content |
|---|---|
| 1 | Type of food eaten as meal and estimation accuracy thereof |
| 2 | Number of times of chewing per meal |
| 3 | Meal time |
| 4 | Estimated value of occlusal force at the time of eating a certain food and accuracy thereof |
| 5 | Advice on meal content (for example, the number of times of chewing is low and the user does not eat rice) |
| 6 | Interval between breakfast, lunch, and dinner |
| 7 | History of type of eaten food (for example, history of each meal for one week) |
| 8 | History of number of times of chewing (for example, history of each meal for one week) |
| 9 | History of meal time (for example, history of each meal for one week) |
| 10 | Evaluation of recent meal trend with respect to standard dietary habits (for example, whether or not the meal has improved recently) |

TABLE 1-continued

| Item No. | Content |
|---|---|
| 11 | Advice for improving dietary habits (for example, it is recommended to increase the number of times of chewing, it is recommended to keep a meal time constant, it is recommended to increase a meal time, or it is recommended to eat harder food) |
| 12 | How long has it been since previous washing |
| 13 | Posture at the time of meal |
| 14 | State of jaw movement at the time of chewing (for example, estimation operation for an occlusal cycle and a kinetic condyle point at a lower jaw joint projection) (displayed for each chewed food) |
| 15 | Recent change in jaw movement at the time of chewing (for example, estimation operation for an occlusal cycle, and a kinetic condyle point at the lower jaw joint projection) |

Processing Flow of Dietary Habits Assessment Device

Figure 10:
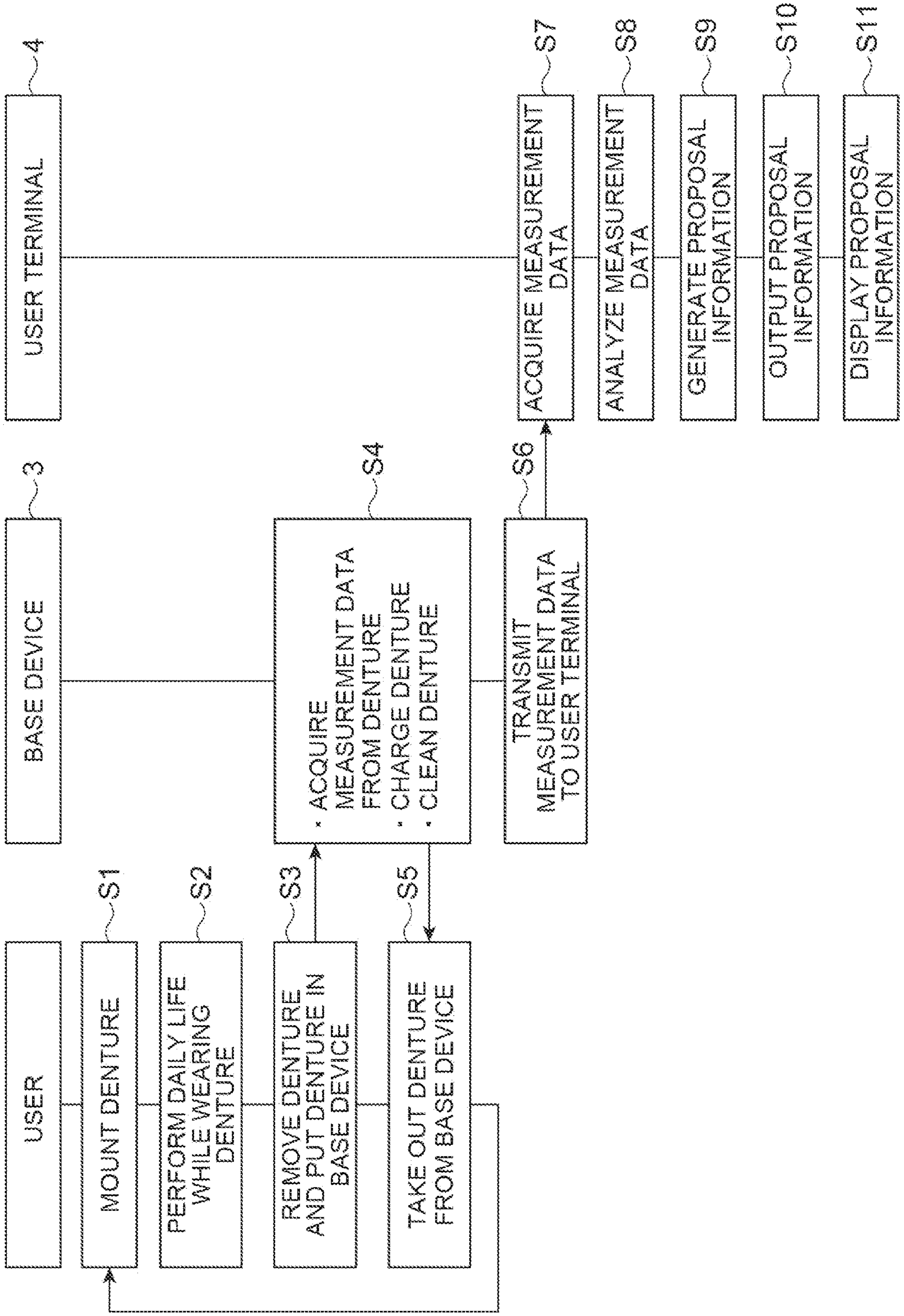
FIG. 10 is a flow chart illustrating an example processing flow of the dietary habits assessment system.

FIG. 10 is a diagram illustrating an example of a processing flow of the dietary habits assessment system 1. As illustrated in FIG. 10, first, the denture 2 is mounted by the user (step S1). The user performs daily life while wearing the denture 2 (step S2). The daily life includes a meal period in which the user ingests food. Accordingly, in the sensor 20 of the denture 2, the jaw movement information of the user in a meal period (e.g., the triaxial acceleration data and/or the triaxial angular velocity data acquired by the sensor unit 21) is acquired and stored as measurement data. The user removes the denture 2 from the lower jaw of the user and puts the denture 2 in the storage space 34 of the base device 3 at a timing such as before going to bed (step S3).

Subsequently, the base device 3 acquires the measurement data from the sensor 20 of the denture 2 using the communication unit 32. Further, the base device 3 charges the sensor 20 using the wireless charging antenna 31, and cleans the denture 2 using the cleaning unit 33 (step S4). After processing of step S4 is completed (for example, a timing such as after waking up), the user takes out the denture 2 from the base device 3 (step S5) and mounts the denture 2 again (step S1). On the other hand, the base device 3 transmits the measurement data acquired in a state in which the denture 2 is set in the storage space 34 in step S4 to the user terminal 4 (step S6).

Subsequently, in the user terminal 4, the acquisition unit 41 acquires the measurement data from the base device 3 (step S7). Subsequently, the analysis unit 42 analyzes the measurement data (step S8). For example, the analysis unit 42 identifies the chewing section CS for each bite (see FIG. 6) using the chewing section specifying module 42*a*, and performs, for example, noise removal in each chewing section CS using the filtering and calculation module 42*b*, as illustrated in FIG. 5. Accordingly, the chewing information for each bite (e.g., the time-series data D1 and D2) can be obtained. The time-series data D1 and D2 are examples of the chewing information that is the time-series information indicating the jaw movement for each bite. The analysis unit 42 acquires the analysis result for each bite from the chewing information for one bite using the analysis module 42*c*. The analysis result includes the information obtained by using the analysis model M1, but may further include information obtained without using the analysis model M1. According to examples, the information obtained by using the analysis model M1 includes an attribute of the food determined to be chewed by the user for each bite, and the estimated value of the amount of chewing muscle activity for each bite. The information obtained without using the analysis model M1 is information obtained using, for example, a statistical scheme for the chewing information for each bite and is, for example, information such as the number of times of chewing for each bite, occlusal force for each bite, and a posture for each bite (the posture of the head at the time of eating).

Subsequently, the generation unit 44 generates the proposal information as described above on the basis of the analysis result of the analysis unit 42 (step S9). Subsequently, the output unit 46 outputs the proposal information generated by the generation unit 44 (step S10). According to examples, the output unit 46 outputs display data to the display unit 47. The display unit 47 displays the display data (the proposal information) acquired from the output unit 46 (step S11). Accordingly, the proposal information is presented to the user.

Operations and Effects

The dietary habits assessment system 1 (e.g., the user terminal 4) includes the analysis unit 42. In such a user terminal 4, the attribute of the food determined to have been chewed by the user is acquired by using the analysis model M1 generated by machine learning. Further, the analysis model M1 is generated by machine learning using the training data obtained from past meals of the user who is an analysis target. Accordingly, the analysis result (the attribute of the food determined to have been chewed by the user) may be determined more easily and accurately, by using the analysis model M1 that has learned the characteristics of the jaw movement of the user at the time of eating.

Further, as described above, the analysis model M1 may be the learned model generated by machine learning using the training data including the first chewing information (e.g., the data in the section B1 in FIG. 8) that is the time-series information indicating the jaw movement corresponding to the first chewing operation in the chewing information (the first information), which is time-series information indicating the past jaw movement for one bite acquired for the user, the second chewing information (e.g., the data in the section B2 in FIG. 8) that is the time-series information indicating the jaw movement corresponding to the second chewing operation in the first information, and the information (second information) indicating the attribute of the food chewed according to the past jaw movement for one bite by the user. The analysis unit 42 (the analysis module 42*c*) may acquire the attribute of the food determined to have been chewed according to the jaw movement for one bite by the user by extracting the information (data) corresponding to the first chewing information and the information (data) corresponding to the second chewing information from the chewing information, and inputting the extracted information to the analysis model M1. In particular, characteristics according to the attribute of the chewed food appear more noticeably in the jaw movements corresponding to the first chewing operation and the second chewing operation. Accordingly, the attribute of the food having been chewed by the user may be determined more accurately, by generating the analysis model M1 based on the jaw movement corresponding to the first chewing motion and the second chewing motion.

Further, the user terminal 4 includes the acquisition unit 41 that acquires jaw movement information indicating temporal change in at least one of the acceleration in the triaxial directions and the angular velocity in the triaxial directions detected by the sensor provided in the denture mounted on the lower jaw of the user. The analysis unit 42 (the chewing section specifying module 42*a* and the filtering and calculation module 42*b*) acquires the chewing information on the basis of the jaw movement information. According to this configuration, it is possible to acquire the jaw movement information that is the basis of the chewing information by using the sensor 20 provided in the denture 2 that is mounted on the lower jaw of the user on a daily basis. Further, it is possible to appropriately acquire the jaw movement information while minimizing the burden on the user, by using the sensor 20 provided in the denture 2 worn by the user during daily life, including the time of eating.

Further, the user terminal 4 includes the acquisition unit 41, the analysis unit 42, the generation unit 44, and the output unit 46. Further, the dietary habits assessment system 1 includes the denture 2, and the user terminal 4 that analyzes the measurement data acquired by the sensor 20. In the dietary habits assessment system 1 including the user terminal 4, the proposal information related to eating for the user is generated and output from the analysis result of the jaw movement of the user at the time of eating. This makes it possible to appropriately present eating-related proposal based on the analysis result to the user or the like. Therefore, according to the dietary habits assessment system 1 including the user terminal 4, it is possible to appropriately provide useful information to the user.

In addition, the analysis of the measurement data, the generation of the proposal information, and the display of the proposal information are performed locally (that is, on the user terminal 4), so that the user may receive real-time feedback (presentation of the proposal information). Further, it is not necessary to transmit the measurement data to a server for analyzing the measurement data (for example, a device installed in, for example, a data center that provides a cloud service) or cause the server to execute analysis processing, for example. Therefore, it is possible to curb a communication load, and a processing load of the server.

Further, the measurement data (the jaw movement information) includes information indicating the temporal change in at least one of the acceleration in the triaxial directions and the angular velocity in the triaxial directions detected by the sensor 20 provided in the denture 2 mounted on the lower jaw of the user. According to examples, the measurement data is information (triaxial acceleration data) indicating temporal change in acceleration in the triaxial directions. According to this configuration, it is possible to appropriately acquire, as the measurement data, information indicating temporal change in the acceleration and/or the angular velocity detected by the sensor 20 while minimizing the burden on the user and in a non-intrusive manner, by using the sensor 20 provided in the denture 2 worn by the user during daily life, including the time of eating. For example, in some systems, the amount of chewing muscle activity may be measured by attaching electrodes to an outer skin of the user instead of the inside of the oral cavity of the user, whereas in the above-described examples, it is possible to eliminate a need for attachment of such electrodes by using the sensor 20 provided in the denture 2.

Further, the measurement data is the time-series information of the jaw movement of the user at the time of eating, and the analysis result of the analysis unit 42 includes attribute information indicating the attribute of the food determined to have been chewed by the user at the time of eating. According to examples, the attribute of food is a size, hardness, and type of food. This makes it possible to present, to the user, proposal information according to the attribute of the food determined to have been ingested by the user.

Further, the analysis unit 42 extracts chewing information (e.g., time-series data D1 and D2), which is the time-series information indicating the jaw movement for one bite, from the measurement data. The analysis unit 42 inputs the chewing information to the analysis model M1 generated by machine learning, and acquires the attribute of the food determined to have been chewed according to the jaw movement for one bite by the user, which is output from the analysis model M1, as the attribute information. The analysis model M1 may be a learned model generated by machine learning using training data including chewing information (first information) that is time-series information indicating past jaw movement for one bite acquired for the user, and information (second information) indicating an attribute of food chewed according to a jaw movement for one bite by the user. With the above configuration, it is possible to easily and accurately obtain analysis results (e.g., an attribute of food determined to have been chewed by the user) using the analysis model M1 that has learned characteristics of the jaw movement at the time of eating that is particular to the user. As an example, the analysis model M1 is configured to output the estimated value of the amount of chewing muscle activity for one bite, in addition to the attribute of the food. That is, the analysis model M1 is a learned model generated by machine learning using training data further including a past amount of chewing muscle activity for one bite. That is, an output target of the analysis model M1 and an acquisition target of the analysis unit 42 may be only the attribute information of the food, but may further include the attribute information of the food, and the estimated value of the amount of chewing muscle activity for one bite described above. When the analysis unit 42 also acquires the estimated value of the amount of chewing muscle activity for one bite, the training data is configured to include the amount of chewing muscle activity for one bite as the second information.

Further, the user terminal 4 includes the display unit 47 that displays the proposal information output by the output unit 46. It is possible to appropriately present the proposal content according to the analysis result to the user by causing the display unit 47 to display the proposal information (for example, a part or all of information corresponding to the display items shown in Table 1 above).

Further, the dietary habits assessment system 1 includes the base device 3 that stores the denture 2 removed from the lower jaw of the user. The base device 3 includes the communication unit 32 that acquires the measurement data from the sensor 20 by communicating with the sensor 20 and transmits the measurement data to the user terminal 4 by communicating with the user terminal 4. According to the above configuration, the user may set the denture 2 in the base device 3, such that the measurement data is automatically transmitted from the base device 3 to the user terminal 4. This makes it possible to improve the convenience for the user in connection with the acquisition (uploading) of the measurement data from the sensor 20 provided in the denture 2.

Further, the base device 3 further includes the wireless charging antenna 31 that charges the sensor 20. According to the above configuration, it is possible to perform charging using the wireless charging antenna 31 together with communication using the communication unit 32. This makes it possible for power of the sensor consumed during the communication operation using the communication unit 32 to be appropriately supplemented.

Further, the base device 3 further includes the cleaning unit 33 that cleans the denture 2. According to the above configuration, the user can perform both transmission of the measurement data to the user terminal 4 and cleaning of the denture 2 by setting the denture 2 in the base device 3. This makes it possible to improve the convenience for the user.

Although various examples have been described above, the present disclosure is not limited to the above-described examples.

For example, although a terminal (the user terminal 4) of a user who wears the denture 2 is described as forming the dietary habits assessment device, the dietary habits assessment device may be provided by a terminal device different from the user terminal 4. For example, the dietary habits assessment device (e.g., the user terminal 4) described above may be a terminal of the attending physician of the user (for example, a terminal in a hospital or clinic). In this case, the base device 3 may be provided in the hospital. For example, when the user visits the hospital on a regular basis, it is possible to upload the measurement data to the terminal of the attending physician by setting the denture 2 in the base device 3. Further, in medical examination, the attending physician can give advice regarding eating to the user while referring to the analysis result for the measurement data and proposal information according to the analysis result on the terminal.

Figure 11:
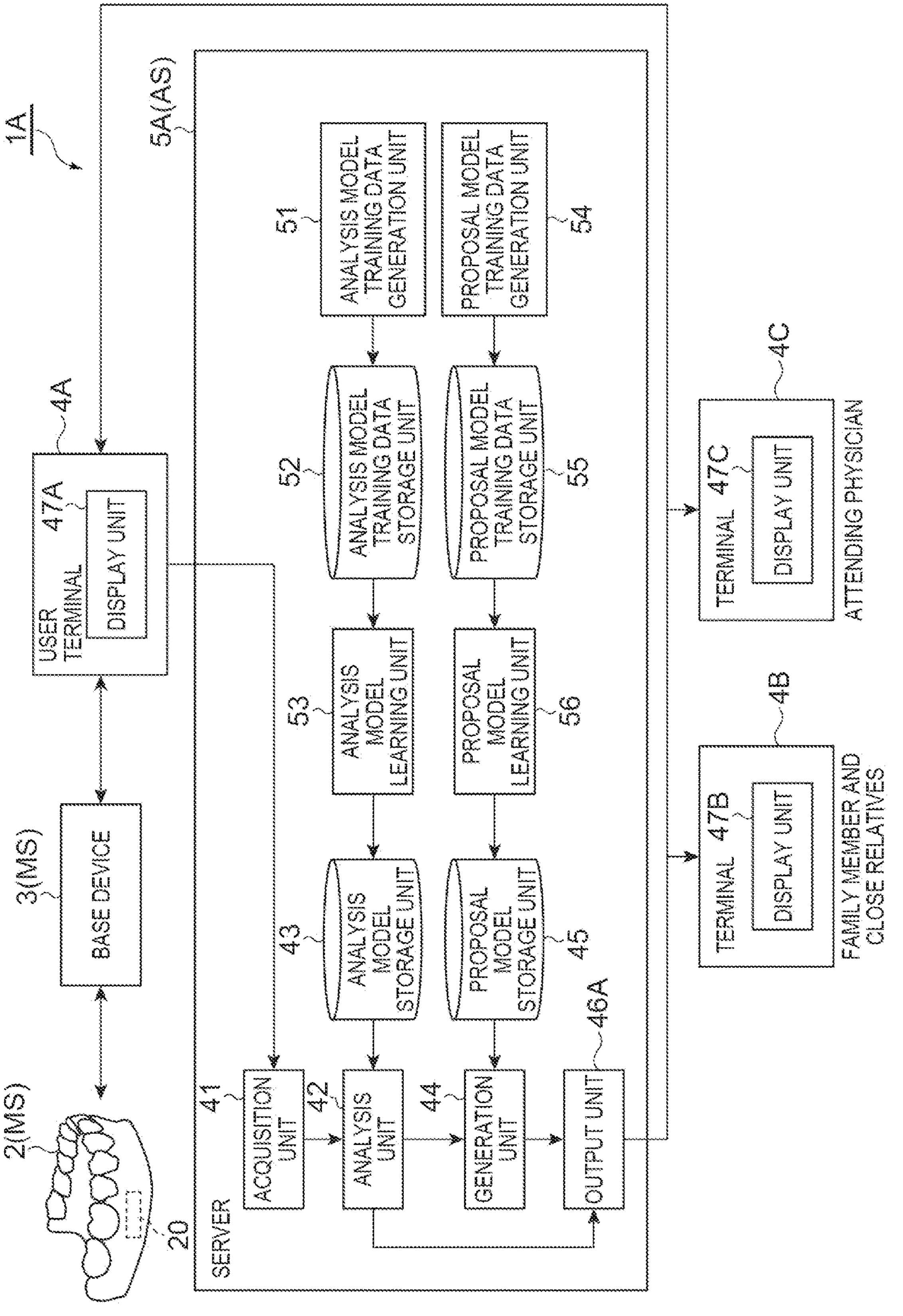
FIG. 11 is a block diagram illustrating a configuration of a dietary habits assessment system according to an example.

Further, a function of the dietary habits assessment device (particularly the user terminal 4) described above may be configured on a server, as in a dietary habits assessment device 1A (also referred to herein as a "dietary habits assessment system" or "dietary habits estimation system") according to a modification example illustrated in FIG. 11. The dietary habits assessment system 1A differs from the dietary habits assessment system 1 in that a user terminal 4A and a server 5A are included in place of the user terminal 4 and the server 5. For example, in the dietary habits assessment system 1A, some (the acquisition unit 41, the analysis unit 42, the analysis model storage unit 43, the generation unit 44, and the proposal model storage unit 45) of the functions included in the user terminal 4 are included in the server 5A. The server 5A includes an output unit 46A. The user terminal 4A includes a display unit 47A similar to the display unit 47. In the dietary habits assessment system 1A, the calculation device AS is provided by the server 5A.

The user terminal 4A is configured to transmit the measurement data to the server 5A without performing analysis processing on the measurement data when the user terminal 4A acquires the measurement data from the base device 3. The server 5A is configured to execute the analysis of the measurement data, and the generation of the proposal information based on the analysis result, similar to the user terminal 4 described above.

The output unit 46A may notify the user terminal 4A owned by the user who wears the denture 2 of the proposal information. Accordingly, the proposal information notified of from the output unit 46A is displayed on the display unit 47A of the user terminal 4A. According to the above configuration, the dietary habits assessment device may be provided by, for example, the server 5A on the cloud, so as to appropriately present the proposal information to the user.

Further, the output unit 46A may notify a terminal owned by another user different from the user wearing the denture 2, which has been set as a notification destination in advance, of the proposal information. For example, the server 5A may register and store, for each user, contact information (for example, an e-mail address) of another user associated with the user in advance. In the present example, a terminal 4B and a terminal 4C are set as notification destinations. The terminal 4B is a terminal that is owned by another user who is a family member or a close relative of the user. The terminal 4C is a terminal that is owned by another user who is an attending physician of the user. Accordingly, the proposal information notified of from the output unit 46A is displayed on each of a display unit 47B of the terminal 4B and a display unit 47C of the terminal 4C. According to the above configuration, the other user can ascertain an eating situation of the user. This makes it possible for a family member, close relative, attending physician, or the like of the user to realize monitoring of an eating situation of the user.

In a case in which the user leaves the denture 2 on for a long period, the analysis of the measurement data and the generation of the proposal information in the server 5A are not executed and notifying the family member, close relative, attending physician, or the like of the user of the proposal information is not performed, such that the above monitoring is not appropriately realized. Therefore, for example, when a state in which proposal information for a certain user is not generated lasts for a predetermined period or more, the server 5A (for example, the output unit 46A) may notify the terminals 4B and 4C of the other users associated with the user in advance of the fact. Further, such a notification may be made by the base device 3 or the user terminal 4A. For example, when a state in which the denture 2 is not set in the storage space 34 of the base device 3 lasts for a predetermined period or more after the denture 2 is previously set in the storage space 34 of the base device 3 and communication, charging, cleaning, and the like are performed, the base device 3 may notify the terminals 4B and 4C of the other users of the fact. Similarly, when a state in which the measurement data cannot be acquired from the base device 3 lasts for a predetermined period or more, the user terminal 4A may notify the terminals 4B and 4C of the other users of the fact. Further, the user terminal 4A may display notification information for encouraging the user to set the denture 2 on the base device 3 on the display unit 47A.

Additionally, the analysis model M1 may be prepared for each user. That is, the analysis model M1 is generated on the basis only on training data obtained from an eating operation performed in the past by the user who is an analysis target. However, the analysis model M1 may be a learned model generated by machine learning using training data including chewing information (first information) indicating past jaw movement for one bite acquired for an unspecified user (a user wearing a denture provided with a sensor, like the denture 2) and an attribute (second information) of food chewed according to the past jaw movement for one bite by the unspecified user. That is, the training data used for learning of the analysis model M1 may be obtained from eating operations performed by a plurality of unspecified users in advance. In a case in which the training data is obtained from the eating operations performed by the plurality of unspecified users in the past (or in advance), when a certain user becomes an analysis target, learning may be performed so that an analysis result corresponding to the second information most applicable to the user in the first information is output. In this case, the analysis model M1 can be shared among a plurality of users. Accordingly, it is not necessary to create and manage the analysis model M1 for each user. Further, it is easier to collect training data for the analysis model M1, as compared with a case in which the analysis model M1 is prepared for each user separately.

Figure 12:
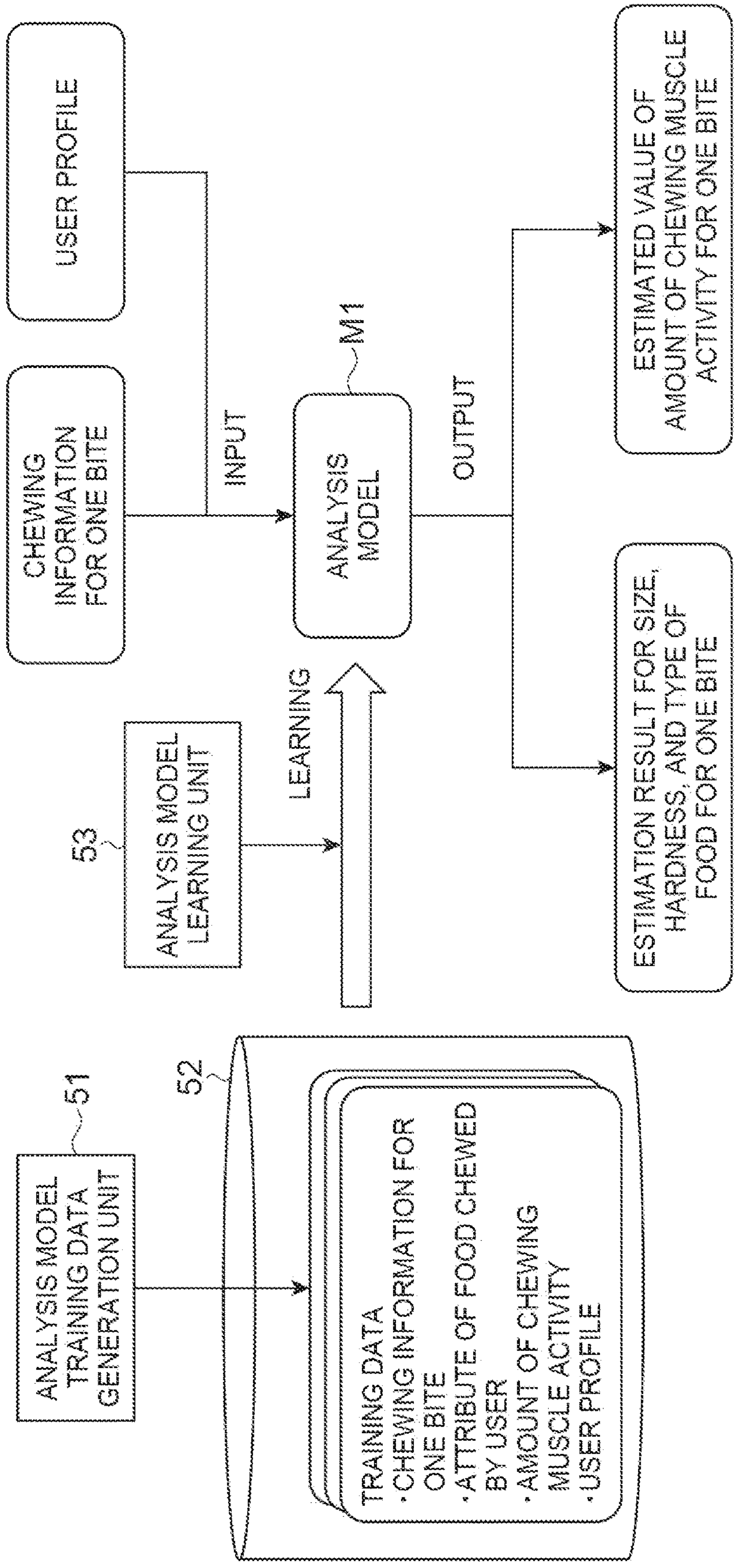
FIG. 12 is a schematic diagram illustrating an overview of an analysis model according to the example of FIG. 11.

Further, as illustrated in FIG. 12, the analysis model M1 may be a learned model that has been generated by machine learning using training data further including a user profile indicating an attribute of an unspecified user. In this case, the analysis unit 42 is configured to further input a user profile (profile information) indicating an attribute of a user (a user who is an analysis target) to the analysis model M1. Here, the attribute of the user is, for example, sex, age (or year), and health condition. It is conceivable that the jaw movement of the user at the time of eating depends on such attribute of the user. Accordingly, the attribute of the food having been chewed by the user may be determined more accurately by taking into consideration the attribute of the user.

Further, the analysis result may include an opening amount indicating the size of opening of the mouth of the user at the time of eating. Such an opening amount can be ascertained from, for example, the waveform of the chewing information (the time-series data D3 in FIG. 9) described above. The generation unit 44 may generate proposal information including information on the necessity of diagnosis of temporomandibular joint disease on the basis of the opening amount. For example, the generation unit 44 acquires a maximum value (or an average value or the like) of the opening amount of the user in the predetermined period from the analysis result corresponding to the predetermined period (for example, for one day) and compares the maximum value with a predetermined threshold value. The generation unit 44 may determine that there is a risk of temporomandibular joint disease when the maximum value is less than the threshold value, and generate proposal information for encouraging a diagnosis of temporomandibular joint disease. According to such a configuration, it is possible to make a proposal for encouraging the user or the like suspected of having the temporomandibular joint disease to make an early diagnosis on the basis of the size of opening of the mouth of the user at the time of eating.

Further, the generation unit 44 may hold information on a usual meal amount of the user in advance, calculate a total meal amount of the user in a predetermined period from an analysis result corresponding to the predetermined period (mainly a size of food estimated for each bite), compare the total meal amount with the usual meal amount, and generate proposal information according to a comparison result. For example, when the total meal amount is less than the usual meal amount by a predetermined threshold value or more, the generation unit 44 may determine that there is a risk of a disease of the stomach or intestine, and generate proposal information for encouraging the user to check a condition of the stomach or intestine. Alternatively, when the total meal amount is greater than the usual meal amount by a predetermined threshold value or more, the generation unit 44 may determine that the user has overeaten, and generate proposal information for encouraging the user to curb the meal amount.

Further, for example, when the user wears a complete denture, the denture mounted on the upper jaw may be provided with the same sensor as the sensor 20 of the denture 2 mounted on the lower jaw described above. The measurement data acquired by the acquisition unit 41 may include information indicating the temporal change in at least one of the acceleration in the triaxial directions and the angular velocity in the triaxial directions (hereinafter referred to as "upper jaw measurement data") detected by the sensor provided in the denture mounted on the upper jaw of the user, together with measurement data detected by the sensor 20 (hereinafter referred to as "lower jaw measurement data"). For example, when the user is in a vehicle such as a car or a train, there is concern that a vibration component from the vehicle is detected by the sensor 20, and erroneously detected as a jaw movement of the user at the time of eating. Further, when the user eats while being in the vehicle, the vibration component from the vehicle is incorporated as noise into the jaw movement of the user at the time of eating. On the other hand, according to the above configuration, the analysis unit 42 can perform analysis using not only a detection result of the sensor 20 provided in the denture 2 mounted on the lower jaw of the user, but also a detection result of the sensor provided in the denture mounted on the upper jaw of the user. For example, the chewing section specifying module 42*a* can acquire (extract) only a movement component indicating the jaw movement of the user in the lower jaw measurement data as the chewing information by using not only the lower jaw measurement data but also the upper jaw measurement data. For example, the chewing section specifying module 42*a* can cancel the vibration component from the vehicle (that is, a component commonly contained in both the sensor of the upper jaw and the sensor of the lower jaw) by obtaining a relative value of a detection result of the sensor of the lower jaw (that is, lower jaw measurement data) with respect to a detection result of the sensor of the upper jaw (that is, upper jaw measurement data). As a result, it is possible to solve the above-described problem.

Additionally, the user terminal 4 or the server 5A described above includes an analysis function for acquiring the attribute of the food determined to have been chewed by the user as the analysis result by analyzing the measurement data, and a proposal function for making a proposal based on the analysis result. However, in other examples, the proposal function (that is, the generation unit 44, the proposal model storage unit 45, the output unit 46, the display unit 47, and the like) may be performed by another device from the user terminal 4 or the server 5A.

Figure 13:
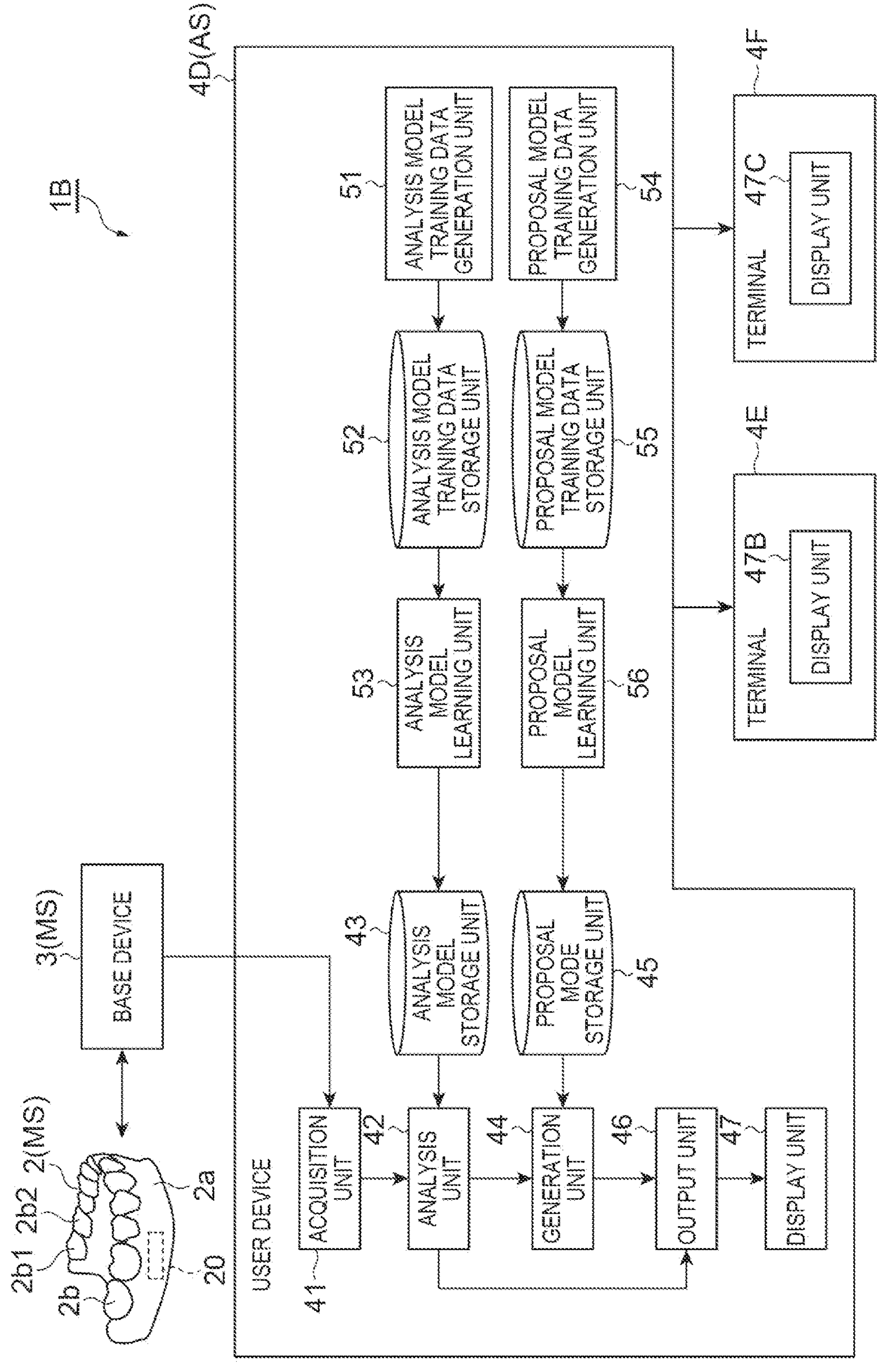
FIG. 13 is a block diagram illustrating a configuration of a dietary habits assessment system according to an example.

Further, the server may be replaced with a user device 4D obtained by adding the function of the server 5 to the user terminal 4 illustrated in FIG. 1, so as to obtain the example dietary habits assessment device 1B (also referred to herein as a "dietary habits assessment system" or "dietary habits estimation system") illustrated in FIG. 13. The user device 4D may be independently provided, for example, at the home of the user, or the like. Alternatively, the user device 4D may communicate, for example, a terminal 4E similar to the terminal 4B illustrated in FIG. 11 and a terminal 4F similar to the terminal 4C illustrated in FIG. 11, information (for example, the information output by the output unit 46) via an arbitrary communication network such as a telephone line and an Internet line. Since respective functions included in the user device 4D, the terminal 4E, and the terminal 4F are the same as the respective functions of the user terminal 4, the server 5, the terminal 4B, and the terminal 4C described above, detailed description thereof will be omitted. When the user device 4D is connected to the terminal 4E and the terminal 4F, it is possible to appropriately notify persons related to the user (for example, a family member or an attending physician) of the proposal information, warnings, and the like. In particular, when a person related to the user is separated from the user, it is possible to detect and deal with a defect that has occurred in the user at an early stage. In the dietary habits assessment system 1B, the calculation device AS is provided by the user device 4D.

Examples described in the present disclosure may also be represented as follows.

Example Aspect 1

A system for executing assessment of dietary habits, including a circuit, the circuit performs analysis for acquiring chewing information, the chewing information being time-series information indicating a jaw movement for one bite at the time of eating of a user, inputting the chewing information to an analysis model generated by machine learning, and acquiring an attribute of food determined to have been chewed according to the jaw movement for one bite by the user, the attribute being output from the analysis model, wherein the analysis model is a learned model generated by machine learning using training data including first information, the first information being time-series information indicating a past jaw movement for one bite acquired for the user, and second information indicating the attribute of the food chewed according to the past jaw movement for one bite by the user.

Example Aspect 2

A system for executing assessment of dietary habits, including a circuit, the circuit performs analysis for acquiring chewing information, the chewing information being time-series information indicating a jaw movement for one bite at the time of eating of a user, inputting the chewing information to an analysis model generated by machine learning, and acquiring an attribute of food determined to have been chewed according to the jaw movement for one bite by the user, the attribute being output from the analysis model, wherein the analysis model is a learned model generated by machine learning using training data including first information, the first information being time-series information indicating a past jaw movement for one bite acquired for an unspecified user, and second information indicating an attribute of food chewed according to the past jaw movement for one bite by the unspecified user.

Example Aspect 3

The system for executing assessment of dietary habits according to example aspect 2, wherein the circuit further inputs profile information indicating an attribute of the user to the analysis model when performing the analysis, and the analysis model is a learned model generated by machine learning using the training data further including profile information of the unspecified user.

Example Aspect 4

The system for executing assessment of dietary habits according to any one of example aspects 1 to 3, wherein the analysis model is a learned model generated by machine learning using training data including data corresponding to first chewing information, the first chewing information being time-series information indicating a jaw movement corresponding to a first chewing operation in the first information, data corresponding to second chewing information, the second chewing information being time-series information indicating a jaw movement corresponding to a second chewing operation in the first information, and the second information, and the circuit acquires the attribute of the food determined to have been chewed according to the jaw movement for one bite by the user, by extracting the first chewing information and the second chewing information from the chewing information and inputting the extracted information to the analysis model, when performing the analysis.

Example Aspect 5

The system for executing assessment of dietary habits according to any one of example aspects 1 to 4, wherein the circuit acquires jaw movement information detected by a sensor provided in a denture mounted on a lower jaw of the user, and acquires the chewing information on the basis of the jaw movement information when performing the analysis.

Example Aspect 6

The system for executing assessment of dietary habits according to example aspect 5, wherein the jaw movement information includes information indicating temporal change in at least one of acceleration in triaxial directions and angular velocity in the triaxial directions detected by the sensor.

Example Aspect 7

The system for executing assessment of dietary habits according to example aspect 6, wherein the jaw movement information further includes information indicating temporal change in at least one of the acceleration in the triaxial directions and the angular velocity in the triaxial directions detected by a sensor provided in a denture mounted on an upper jaw of the user.

Example Aspect 8

The system for executing assessment of dietary habits according to example aspects 1 to 7, wherein the attribute of the food includes at least one of a size, a hardness, and a type of food.

Example Aspect 9

The system for executing assessment of dietary habits according to example aspect 5, further including a base configured to store the denture removed from the lower jaw of the user, wherein the base acquires the jaw movement information from the sensor by communicating with the sensor.

Example Aspect 10

The system for executing assessment of dietary habits according to example aspect 9, wherein the base further includes a charger configured to charge the sensor.

Example Aspect 11

The system for executing assessment of dietary habits according to example aspect 9, wherein the base further includes a washer configured to clean the denture.

Example Aspect 12

A device for executing assessment of dietary habits, including a circuit, the circuit performs analysis for acquiring chewing information, the chewing information being time-series information indicating a jaw movement for one bite at the time of eating of a user, inputting the chewing information to an analysis model generated by machine learning, and acquiring an attribute of food determined to have been chewed according to the jaw movement for one bite by the user, the attribute being output from the analysis model, wherein the analysis model is a learned model generated by machine learning using training data including first information, the first information being time-series information indicating a past jaw movement for one bite acquired for the user, and second information indicating the attribute of the food chewed according to the past jaw movement for one bite by the user.

Example Aspect 13

A device for executing assessment of dietary habits, including a circuit, the circuit performs analysis for acquiring chewing information, the chewing information being time-series information indicating a jaw movement for one bite at the time of eating of a user, inputting the chewing information to an analysis model generated by machine learning, and acquiring an attribute of food determined to have been chewed according to the jaw movement for one bite by the user, the attribute being output from the analysis model, wherein the analysis model is a learned model generated by machine learning using training data including first information, the first information being time-series information indicating a past jaw movement for one bite acquired for an unspecified user, and second information indicating an attribute of food chewed according to the past jaw movement for one bite by the unspecified user.

Example Aspect 14

A method of assessing dietary habits, including, a step of acquiring chewing information, the chewing information being time-series information indicating a jaw movement for one bite at the time of eating of a user, a step of inputting the chewing information to an analysis model generated by machine learning, and a step of performing analysis for acquiring an attribute of food determined to have been chewed according to the jaw movement for one bite by the user, the attribute being output from the analysis model, wherein the analysis model is a learned model generated by machine learning using training data including first information, the first information being time-series information indicating a past jaw movement for one bite acquired for the user, and second information indicating the attribute of the food chewed according to the past jaw movement for one bite by the user.

Example Aspect 15

A method of assessing dietary habits, including, a step of acquiring chewing information, the chewing information being time-series information indicating a jaw movement for one bite at the time of eating of a user, a step of inputting the chewing information to an analysis model generated by machine learning, and a step of acquiring an attribute of food determined to have been chewed according to the jaw movement for one bite by the user, the attribute being output from the analysis model, wherein the analysis model is a learned model generated by machine learning using training data including first information, the first information being time-series information indicating a past jaw movement for one bite acquired for an unspecified user, and second information indicating an attribute of food chewed according to the past jaw movement for one bite by the unspecified user.

It is to be understood that not all aspects, advantages and features described herein may necessarily be achieved by, or included in, any one particular example. Indeed, having described and illustrated various examples herein, it should be apparent that other examples may be modified in arrangement and detail is omitted.

The invention claimed is:

1. A jaw movement analysis system comprising:

circuitry configured to:

acquire chewing information including time-series information that represents a jaw movement of a user chewing food, wherein the jaw movement of the user includes a succession of occlusal cycles for chewing the food, each occlusal cycle spanning from a widening to a closing of a jaw of the user;

extract from the chewing information acquired, first chewing data associated with an initial occlusal cycle from among the succession of occlusal cycles performed by the user, and second chewing data associated with a subsequent occlusal cycle that follows the initial occlusal cycle in the succession of occlusal cycles;

acquire an analysis model that is generated by machine learning based on training data including:

past jaw movement information indicating a past jaw movement during a chewing of food, wherein the past jaw-movement information includes:

first chewing information including time-series information of a first occlusal cycle in the past jaw movement; and second chewing information including time-series information of a second occlusal cycle that follows the first occlusal cycle in the past jaw movement; and food attribute information that indicates an attribute of the food chewed during the past jaw movement associated with the first chewing information and the second chewing information of the past jaw-movement information; and determine an attribute of the food having been chewed by the user based on the analysis model and based on the first chewing data and the second chewing data of the chewing information acquired.

2. The jaw movement analysis system according to claim 1, wherein the past jaw movement is a past jaw movement performed by the user.

3. The jaw movement analysis system according to claim 1, wherein the past jaw movement is a past jaw movement performed by an unspecified user, wherein the training data further includes profile information of the unspecified user, wherein the circuitry is further configured to acquire the profile information, and wherein the attribute of the food is determined additionally based on the profile information acquired.

4. The jaw movement analysis system according to claim 1, further comprising:

a sensor mounted on a denture of the user to detect jaw movement information, wherein the chewing information is acquired based on the jaw movement information detected.

5. The jaw movement analysis system according to claim 4, wherein the circuitry is further configured to:

determine a first waveform from the jaw movement information indicating a temporal change in an acceleration of the sensor in triaxial directions; and determine a second waveform from the jaw movement information indicating a temporal change in an angular velocity of the sensor in the triaxial directions, wherein the first chewing data includes portions of the first waveform and the second waveform associated with the initial occlusal cycle performed by the user, and wherein the second chewing data includes portions of the first waveform and the second waveform associated with the subsequent occlusal cycle performed by the user.

6. The jaw movement analysis system according to claim 5, wherein the sensor is a first sensor mounted on a lower jaw denture of the user, wherein the jaw movement analysis system further includes a second sensor mounted on an upper jaw denture of the user, and wherein the jaw movement information further includes additional information indicating a temporal change in an acceleration in the triaxial directions and in an angular velocity in the triaxial directions, detected by the second sensor mounted on the upper jaw denture of the user.

7. The jaw movement analysis system according to claim 4, further comprising:

a base device forming a storage space configured to accommodate the denture, wherein the denture communicates with the base device through wireless communication to transmit the jaw movement information from the sensor of the denture located in the storage space.

8. The jaw movement analysis system according to claim 7, wherein the base device further includes a charger configured to charge the sensor of the denture located in the storage space.

9. The jaw movement analysis system according to claim 8, wherein the charger is a charging antenna configured to charge the sensor of the denture wirelessly.

10. The jaw movement analysis system according to claim 1, further comprising:

one or more processors including the circuitry, wherein the circuitry includes a storage storing the training data, and wherein the one or more processors are further configured to generate the analysis model from the training data.

11. The jaw movement analysis system according to claim 1, wherein the attribute determined includes a size of the food having been chewed, wherein the circuitry is further configured to:

determine a hardness of the food having been chewed by the user based on the chewing information acquired and based on the analysis model; and identify the food having been chewed based on the size and the hardness, and wherein the jaw movement analysis system further includes a user interface device configured to output user-targeted information based on the food identified.

12. The jaw movement analysis system according to claim 1, wherein the circuitry is further configured to:

determine recommendation information based on the attribute of the food determined; and transmit the recommendation information to be output on a user interface of a terminal device.

13. A non-transitory storage device for jaw movement analysis, the non-transitory storage device comprising processor-readable data and instructions configured to:

acquire chewing information including time-series information that represents a jaw movement of a user chewing food, wherein the jaw movement of the user includes a succession of occlusal cycles for chewing the food, each occlusal cycle spanning from a widening to a closing of a jaw of the user;

extract from the chewing information acquired, first chewing data associated with an initial occlusal cycle from among the succession of occlusal cycles performed by the user, and second chewing data associated with a subsequent occlusal cycle that follows the initial occlusal cycle in the succession of occlusal cycles;

acquire an analysis model that is generated by machine learning based on training data including:

past jaw-movement information indicating a past jaw movement during a chewing of food, wherein the past jaw-movement information includes:

first chewing information including time-series information of a first occlusal cycle in the past jaw movement; and second chewing information including time-series information of a second occlusal cycle that follows the first occlusal cycle in the past jaw movement; and food attribute information that indicates an attribute of the food chewed during the past jaw movement associated with the first chewing information and the second chewing information of the past jaw-movement information; and determine a size of the food having been chewed by the user based on the chewing information acquired and based on the analysis model, wherein the attribute of the food indicated by the food attribute information indicates the size of the food chewed during the past jaw movement associated with the past jaw-movement information.

14. The non-transitory storage device according to claim 13, wherein the processor-readable data and instructions are further configured to:

determine a hardness of the food having been chewed by the user based on the analysis model and based on the first chewing data and the second chewing data associated with the jaw movement of the user; and identify the food having been chewed by the user based on the size and the hardness.

15. The non-transitory storage device according to claim 13, wherein the chewing information is acquired based on jaw movement information detected by at least one sensor mounted on a denture of the user, wherein the jaw movement information detected by the at least one sensor includes information indicating a temporal change in an angular velocity in triaxial directions between an upper jaw and a lower jaw of the user, and wherein the size of the food having been chewed by the user is determined based on the temporal change in the angular velocity.

16. The non-transitory storage device according to claim 13, wherein the past jaw movement associated with the training data from which the analysis model is generated, is selected from the group consisting of: a past jaw movement performed by the user, and a past jaw movement performed by an unspecified user.

17. The non-transitory storage device according to claim 13, wherein the processor-readable data and instructions are further configured to:

determine a hardness of the food having been chewed by the user based on the chewing information acquired and based on the analysis model;

identify the food having been chewed based on the size and the hardness; and transmit the food identified to be output via a user interface device.

18. The non-transitory storage device according to claim 13, wherein the chewing information is acquired by a sensor fixed to the jaw of the user, and indicates a sensor position over time, wherein the past jaw-movement information of the training data includes angular velocity data including time-series information indicating a position of a lower jaw relative to an upper jaw, wherein the analysis model is generated based on the angular velocity data of the training data, and wherein the size of the food having been chewed by the user is determined based on, in addition to the analysis model, the sensor position acquired by the sensor.

* * * * *